United States Patent [19]

Fuhrer et al.

[11] Patent Number: 4,559,354

[45] Date of Patent: Dec. 17, 1985

[54] CERTAIN ANTIHYPERTENSIVE 1-[2-[3-CARBAMOYL-4-HYDROXY PHENOXY]ALKYLENE AMINO]-HETEROCYCLIC PHENOXY-PROPANOL DERIVATIVES

[75] Inventors: Walter Fuhrer, Frenkendorf; Franz Ostermayer; Markus Zimmermann, both of Riehen, all of Switzerland

[73] Assignee: Ciba-Geigy Corporation, Ardsley, N.Y.

[21] Appl. No.: 490,211

[22] Filed: May 6, 1983

Related U.S. Application Data

[63] Continuation of Ser. No. 259,323, Apr. 30, 1981, abandoned.

[30] Foreign Application Priority Data

May 9, 1980 [CH] Switzerland ............... 3655/80

[51] Int. Cl.$^4$ ............... C07D 213/38; C07D 307/52; C07D 333/20; A61K 31/44
[52] U.S. Cl. ............... 514/357; 514/359; 514/427; 514/383; 546/291; 548/255; 548/269; 548/560
[58] Field of Search ............ 548/342, 255, 269, 560; 546/291; 424/263, 273 R, 269; 514/357, 427, 359, 383

[56] References Cited

U.S. PATENT DOCUMENTS 4,134,983  1/1979  Baldwin ........................ 514/400
4,199,580  4/1980  Baldwin ........................ 514/237

OTHER PUBLICATIONS

Baldwin, J. Med. Chem., 22, 687–694 (1979).

Primary Examiner—Alan L. Rotman
Attorney, Agent, or Firm—Irving N. Feit

[57] ABSTRACT

The invention relates to novel substituted phenyl ethers of the formula

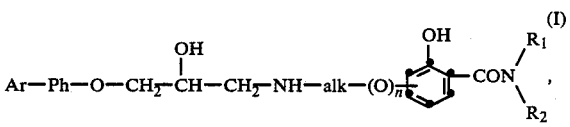

in which Ar represents a mono- or bi-cyclic carbocyclic aryl radical, or a mono- or bi-cyclic heterocyclic aryl radical bonded to a phenylene radical by way of a ring carbon atom, Ph represents a phenylene radical, n has the value 0 to 1 and alk represents alkylene having from 2 to 5 carbon atoms, the nitrogen atom and the oxygen atom or, if n is 0, the aromatic radical being separated from each other by at least two carbon atoms in the unbranched chain, and $R_1$ and $R_2$ each represents, independently of the other, hydrogen or lower alkyl, or together represent lower alkylene, oxa-lower alkylene, thia-lower alkylene, aza-lower alkylene or N-lower alkyl-aza-lower alkylene, and salts thereof, especially pharmaceutically acceptable non-toxic acid addition salts. Such compounds possess, on the one hand, blocking properties towards β-adrenergic receptors and can therefore be used as β-receptor-blockers with or without cardioselectivity for the treatment of *Angina pectoris,* hypertrophic cardiomyopathy and heart rhythm disorders and also as blood-pressure-reducing agents. On the other hand, such compounds possess β-receptor-stimulating properties and can therefore be used as positively inotropically active agents, especially as cardiotonics, for the treatment of heart muscle insufficiency.

10 Claims, No Drawings

CERTAIN ANTIHYPERTENSIVE 1-[2-[3-CARBAMOYL-4-HYDROXY PHENOXY]ALKYLENE AMINO]-HETEROCYCLIC PHENOXY-PROPANOL DERIVATIVES

This application is a continuation of application Ser. No. 259,323, filed Apr. 30, 1981 abandoned.

The invention relates to novel substituted phenyl ethers, a process for their manufacture, pharmaceutical preparations containing such compounds, and their use for the manufacture of pharmaceutical preparations or as pharmacologically active compounds.

The invention relates to novel substituted phenyl ethers of the formula

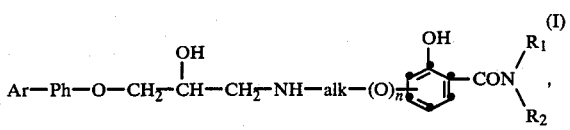

in which
Ar represents a mono- or bi-cyclic carbocyclic aryl radical, or a mono- or bi-cyclic heterocyclic aryl radical bonded to the phenylene radical by way of a ring carbon atom,
Ph represents a phenylene radical,
n has the value 0 or 1 and
alk represents alkylene having from 2 to 5 carbon atoms, the nitrogen atom and the oxygen atom or, if n is 0, the aromatic radical being separated from each other by at least two carbon atoms in the unbranched chain, and
$R_1$ and $R_2$ each represents, independently of the other, hydrogen or lower alkyl, or together represent lower alkylene, oxa-lower alkylene, thia-lower alkylene, aza-lower alkylene or N-lower alkyl-aza-lower alkylene.

The invention relates also to N-oxides of heterocycles and to salts of compounds of the formula I.

The radical Ar is a monocyclic aromatic hydrocarbon radical, i.e. phenyl, but may also represent a bicyclic aromatic hydrocarbon radical, i.e. 1- or 2-naphthyl or partially saturated naphthyl, such as 1,2,3,4-tetrahydro-5-naphthyl. As mono- or bi-cyclic heteroaryl, Ar represents a radical that has preferably 5 or 6 ring members, is bonded to the phenylene radical Ph by way of a ring carbon atom, contains an oxygen, sulphur or nitrogen atom and optionally from 1 to 3 additional nitrogen atoms as ring members and that may be at least partially hydrogenated and, in that case, may be substituted by oxo, wherein, in a bicyclic heterocyclic radical, the second ring may be a fused-on benzo ring, and represents especially pyridyl, for example 2-, 3- or 4-pyridyl or dihydro-oxo-pyridinyl, for example 1,6-dihydro-6-oxo-2-pyridinyl, pyridazinyl, for example 3-pyridazinyl, pyrazinyl, for example 2-pyrazinyl, pyrimidinyl, for example 2-, 4- or 5-pyrimidinyl, or dihydro-oxo-pyrimidinyl, for example 3,4-dihydro-4-oxo-2-pyrimidinyl, furyl, for example 2- or 3-furyl, pyrryl, for example 2- or 3-pyrryl, thienyl, for example 2- or 3-thienyl, oxazolyl, for example 2- or 4-oxazolyl, thiazolyl, for example 2-, 4- or 5-thiazolyl, thiadiazolyl, for example 1,2,4-thiadiazol-3- or -5-yl or 1,2,5-thiadiazol-3-yl, imidazolyl, for example imidazol-2- or -4-yl, pyrazolyl, for example 3- or 4-pyrazolyl, triazolyl, for example 1,2,3-triazol-4-yl or 1,2,4-triazol-3-yl, tetrazolyl, such as tetrazol-5-yl, or indolyl, for example indol-4-yl, quinolinyl, for example 2-quinolinyl, isoquinolinyl, for example 1-isoquinolinyl, benzimidazolyl, for example 2-benzimidazolyl, benzofuranyl, for example 4- or 5-benzofuranyl, benzthiophene, for example 4- or 5-benzthiophene, or naphthyridinyl, for example 1,8-naphthyridin-2-yl.

Substituents of a carbocyclic or heterocyclic aryl radical, wherein, in the latter case, especially a ring carbon atom but also a secondary ring nitrogen atom can be substituted and one or more, but preferably not more than four, of such substituents can be present, are, for example, optionally substituted aliphatic hydrocarbon radicals, such as optionally substituted lower alkyl, for example lower alkyl, optionally etherified or esterified hydroxy-lower alkyl, such as hydroxy-lower alkyl, lower alkoxy-lower alkyl or halo-lower alkyl, or optionally substituted, such as acylated, amino-lower alkyl, such as lower alkanoylamino-lower alkyl or lower alkoxycarbonylamino-lower alkyl, or lower alkenyl or lower alkynyl, optionally etherified or esterified hydroxy or mercapto, such as hydroxy, or lower alkoxy optionally substituted, for example by aryl, by optionally etherified or esterified hydroxy or mercapto or by acyl, for example lower alkoxy, phenyl-lower alkoxy, hydroxy-lower alkoxy, lower alkoxy-lower alkoxy, lower alkylthio-lower alkoxy, halo-lower alkoxy or lower alkanoyl-lower alkoxy, or lower alkenyloxy, lower alkynyloxy, lower alkylthio or halogen, acyl, for example lower alkanoyl, optionally esterified carboxy, such as carboxy or lower alkoxycarbonyl, amidated carboxy, for example optionally substituted carbamoyl, such as carbamoyl, N-lower alkylcarbamoyl or N,N-di-lower alkylcarbamoyl, cyano, nitro or optionally substituted, such as acylated, amino, for example, lower alkanoylamino, lower alkoxycarbonylamino, lower alkylsulphonyl, optionally substituted ureido, also amino, N-lower alkylamino or N,N-di-lower alkylamino. Substituents of a heterocyclic aryl radical Ar are, in addition, aryl, especially phenyl, or aroyl, especially benzoyl, each optionally substituted by lower alkyl, lower alkoxy, halo-lower alkyl, carbamoyl or by cyano, or heterocyclic aryl radicals, for example those mentioned, optionally substituted, for example as stated, which are bonded to a ring carbon atom or a ring nitrogen atom of the heterocyclic aryl radical to be substituted.

Bivalent substituents in a monocyclic, carbocyclic, aromatic hydrocarbon radical, for example phenyl, or in a monocyclic heteroaryl radical, for example imidazole, which are bonded to two ring carbon atoms, are lower alkylene or lower alkenylene.

The radicals and compounds designated "lower" within the context of the present description contain preferably up to 7, and especially up to 4, carbon atoms.

Lower alkyl is, for example, methyl, ethyl, n-propyl, isopropyl, n-butyl, isobutyl or tert.-butyl; substituted lower alkyl is especially corresponding methyl or 1- or 2-ethyl.

Lower alkenyl is, for example, vinyl, allyl, 2- or 3-methallyl or 3,3-dimethylallyl.

Lower alkynyl is especially propargyl.

Lower alkoxy is, for example, methoxy, ethoxy, n-propoxy, isopropoxy, n-butoxy or isobutoxy, whilst phenyl-lower alkoxy is, for example, benzyloxy or 1- or 2-phenylethoxy, lower alkenyloxy is, for example, allyloxy, 2- or 3-methallyloxy or 3,3-dimethylallyloxy and lower alkynyloxy is especially propargyloxy.

Lower alkylthio is, for example, methylthio, ethylthio, n-propylthio or isopropylthio.

Lower alkylsulphonyl is, for example, methylsulphonyl or ethylsulphonyl.

Halogen is preferably halogen having an atomic number of up to 35, i.e. fluorine, chlorine or bromine.

Lower alkanoyl is, for example, acetyl, propionyl or butyryl.

Lower alkoxycarbonyl is, for example, methoxycarbonyl or ethoxycarbonyl.

Optionally substituted carbamoyl is, for example, carbamoyl, or N-lower alkylcarbamoyl or N,N-di-lower alkylcarbamoyl, such as N-methylcarbamoyl, N,N-dimethylcarbamoyl, N-ethylcarbamoyl or N,N-diethylcarbamoyl.

Lower alkanoylamino is, for example, acetylamino or propionylamino.

Lower alkoxycarbonylamino is, for example, methoxycarbonylamino or ethoxycarbonylamino.

Optionally substituted ureido is, for example, ureido or 3-lower alkylureido or 3-cycloalkylureido, in which cycloalkyl has, for example, from 5 to 7 ring members, for example 3-methylureido, 3-ethylureido or 3-cyclohexylureido.

N-lower alkylamino and N,N-di-lower alkylamino are, for example, methylamino, ethylamino, dimethylamino or diethylamino.

Hydroxy-lower alkyl is preferably hydroxymethyl, or 1- or especially 2-hydroxyethyl.

Lower alkoxy-lower alkyl is preferably lower alkoxymethyl, or 1- or especially 2-lower alkoxyethyl, for example methoxymethyl, ethoxymethyl, 2-methoxyethyl or 2-ethoxyethyl.

Halo-lower alkyl is preferably halomethyl, for example trifluoromethyl.

Lower alkanoylamino-lower alkyl is especially lower alkanoylaminomethyl, or 1- or especially 2-lower alkanoylaminoethyl, for example acetylaminomethyl, 2-acetylaminoethyl or 2-propionylaminoethyl.

Lower alkoxycarbonylamino-lower alkyl is especially lower alkoxycarbonylaminomethyl, or 1- or especially 2-lower alkoxycarbonylaminoethyl, for example methoxycarbonylaminomethyl, 2-methoxycarbonylaminoethyl or 2-ethoxycarbonylaminoethyl.

Lower alkoxy-lower alkoxy is, inter alia, lower alkoxymethoxy, or 1- or especially 2-lower alkoxyethoxy, for example methoxymethoxy, 2-methoxyethoxy or 2-ethoxyethoxy.

Lower alkylthio-lower alkoxy is especially lower alkylthiomethoxy, or 1- or especially 2-lower alkylthioethoxy, for example 2-methylthioethoxy or 2-ethylthioethoxy.

Halo-lower alkoxy is especially 2-haloethoxy, for example 2-chloroethoxy.

Lower alkanoyl-lower alkoxy is, for example, lower alkanoylmethoxy or 1- or 2-lower alkanoylethoxy, for example acetylmethoxy.

Lower alkylene as a substituent of a carbocyclic aryl radical Ar is, for example, 1,3-propylene or 1,4-butylene, whilst lower alkenylene is, for example 1,3-prop-1-enylene, 1,4-but-1-enylene or 1,3-butadienylene. A radical of this kind together with a phenyl radical Ar forms, for example, an indanyl, 1,2,3,4-tetrahydronaphthyl, naphthyl or indenyl group which is optionally substituted by way of an aromatic ring carbon atom, whereas, for example, together with a monocyclic heteroaryl group, such as one of those mentioned, for example imidazole, for example, a 1,6-dihydrocyclopenta[d-]imidazole, 4,5,6,7-tetrahydrobenzimidazole or benzimidazole group is formed.

Substituents in a monocyclic heterocyclic aryl radical Ar, for example those mentioned, such as pyridyl, primidinyl, furyl, pyrryl, thienyl, thiadiazolyl, indolyl, quinolyl, imidazolyl or benzimidazolyl are also monocyclic heteroaryl radicals, for example those mentioned, which are optionally substituted, for example as mentioned.

Radicals Ar substituted in this manner are, for example, pyridylphenyl, for example lower alkyl-, such as (methyl-2-pyridyl)-phenyl, (cyano-2-pyridyl)-phenyl, pyrimidinylphenyl, such as (2-pyrimidinyl)-phenyl or (hydroxy-2-pyrimidinyl)-phenyl, furylphenyl, for example lower alkoxy-, such as methoxy-furyl-(2)-phenyl, pyrrylphenyl, such as pyrrol-2-yl- or -3-ylphenyl, for example halo-lower alkyl-, such as trifluoromethylpyrrol-2-yl or -3-ylphenyl, imidazolylphenyl, for example halo-lower alkyl-, such as trifluoromethylimidazol-2-ylphenyl, imidazolylfuryl, for example halo-lower alkyl-, such as (trifluoromethyl)-imidazol-2-ylfuryl, pyrimidinylfuryl, for example hydroxy-2-pyrimidinylfuryl, pyrrylfuryl, for example halo-, such as chloropyrrol-3-ylfuryl, thienylfuryl, for example lower alkyl-, such as methyl-2-thienylfuryl, thiadiazolylfuryl, for example 1,2,4-thiadiazol-3-ylfuryl, indolylfuryl, such as lower alkoxy-, for example 4-methoxyindol-2-ylfuryl, benzimidazolylfuryl, for example lower alkyl-, such as 4-methylbenzimidazol-2-ylfuryl, triazolylfuryl, such as 1,2,4-triazol-3-ylfuryl, tetrazolylfuryl, such as tetrazol-5-ylfuryl, pyrazolylfuryl, such as pyrazol-3-yl- or -4-ylfuryl, quinolinylfuryl, for example lower alkoxy-, such as methoxy-2-quinolinylfuryl, thienylimidazolyl, for example lower alkoxy-, such as (methoxy-2-thienyl- or -3-thienyl)-imidazolyl, thiazolylimidazolyl, for example halo-, such as chlorothiazol-2-ylimidazolyl or 1,2,5-thiadiazol-3-ylimidazolyl.

A phenylene radical Ph is a 1,2-, 1,3- or especially a 1,4-phenylene radical that may contain from 1 to 3 substituents. Substituents are especially lower alkyl, such as methyl, lower alkoxy, such as methoxy, halogen, for example chlorine, halo-lower alkyl, for example trifluoromethyl, optionally functionally modified carboxy, such as carboxy, lower alkoxycarbonyl, for example methoxycarbonyl, carbamoyl, N-lower alkylcarbamoyl, such as N-methylcarbamoyl, N,N-di-lower alkylcarbamoyl, such as N,N-dimethylcarbamoyl, lower alkanoyl, for example acetyl, or cyano or nitro.

Alkylene alk may be straight chain or branched and is, for example, 1,2-ethylene, 1,2-, 2,3- or 1,3-propylene, 1,4- or 2,4-butylene, 2-methyl-2,4-butylene or 1,1-dimethylethylene.

Together with the nitrogen atom of the amide group, $R_1$ and $R_2$, as lower alkylene, are, for example, 1-aziridinyl, 1-azetidinyl, 1-pyrrolidinyl, piperidino, hexahydro-1H-azepin-1-yl; as oxa-lower alkylene, for example, morpholino; as thia-lower alkylene, for example, thiomorpholino; as optionally N-lower alkylated aza-lower alkylene, for example, N-lower alkyl-1-piperazinyl, such as N-methyl-1-piperazinyl, or hexahydro-1H-1,4-diazepin-1-yl.

The aliphatic side chain may substitute the salicylamide ring in any position, but preferably in the paraposition to the carbamoyl group, especially in the paraposition to the hydroxy group.

N-oxides are derived from those compounds in which Ar represents mono- or bi-cyclic heteroaryl containing at least one tertiary nitrogen atom, for example pyridyl, pyrazinyl, pyrimidinyl, imidazolyl, benzimidazolyl, quinolinyl, pyrazolyl, triazolyl, tetrazolyl, thiazolyl or thiadiazolyl.

The novel compounds may be in the form of their salts, such as their acid addition salts and, especially, their pharmaceutically acceptable non-toxic acid addition salts. Suitable salts are, for example, those with inorganic acids, such as hydrohalic acids, for example hydrochloric acid or hydrobromic acid, sulphuric acid, or phosphoric acid, or with organic acids, such as aliphatic, cycloaliphatic, aromatic or heterocyclic carboxylic or sulphonic acids, for example formic, acetic, propionic, succinic, glycolic, lactic, malic, tartaric, citric, maleic, hydroxymaleic, pyruvic, fumaric, benzoic, 4-aminobenzoic, anthranilic, 4-hydroxybenzoic, salicylic, embonic, methanesulphonic, ethanesulphonic, 2-hydroxyethanesulphonic, ethylenesulphonic, toluenesulphonic, naphthalenesulphonic or sulphanilic acid, or with other acidic organic substances, such as ascorbic acid.

The novel compounds of the formula I have valuable pharmacological properties. In particular, they act in a specific manner on $\beta$-adrenergic receptors. This action can be attributed, as a property held in common, to their affinity to those receptors, which manifests itself as a pure blockade when the inherent stimulating action of the receptors is absent or very slight, as a blockade with simultaneous ISA, i.e. intrinsic sympathomimetic activity, when the inherent action of the receptors is slightly to moderately stimulating, and as predominant stimulation of the $\beta$-adrenergic receptors when the inherent action of the latter is relatively strong. The boundaries between $\beta$-receptor blockers without ISA or with more or less pronounced ISA are fluid, just as the therapeutic areas of use of these types of compounds are.

Both in the case of compounds having predominantly $\beta$-blocking properties and in the case of those having predominantly $\beta$-stimulating properties, there may be marked differences in their affinity to cardiac ($\beta_1$-) and to vascular or tracheobronchial ($\beta_2$-) receptors. Finally, added to this, there may also be blood-pressure-reducing and bradycardic actions and also blocking actions on $\alpha$-adrenergic receptors and stimulating actions on dopaminergic receptors.

Of the compounds of the formula I, for example 1-[2-(3-carbamoyl-4-hydroxyphenoxy)-ethylamino]-3-[4-[1-methyl-4-(trifluoromethyl)-1H-imidazol-2-yl]-phenoxy]-2-propanol exhibits as its principal action a blocking action on $\beta$-receptors with clearly preferential inhibition of cardiac receptors, together with the additional activities of a bradycardic and blood-pressure-reducing action and also a weak blocking action on $\alpha$-receptors and stimulating actions on dopaminergic receptors.

In other compounds of the formula I, both $\beta$-receptor-blocking and, above all, $\beta$-receptor-stimulating actions can be detected. These compounds have been found to be, on the one hand in in vitro experiments on the hearts of guinea pigs, potent blockers of cardiac $\beta$-receptors and, on the other hand in in vivo experiments on narcotised cats, strongly active, predominantly $\beta$-receptor-stimulating compounds with additional $\beta$-receptor-blocking properties. This latter group includes, for example, those compounds in which Ar represents a heteroaryl radical having an -NH-group as ring member.

Thus, for example, with 1-[2-(3-carbamoyl-4-hydroxyphenoxy)-ethylamino]-3-[4-[(4-trifluoromethyl)-1H-imidazol-2-yl]-phenoxy]-2-propanol in in vivo experiments on cats, a stimulation of $\beta$-receptors has been observed. As additional actions, it is possible to detect, with compounds of that kind, a reduction in blood pressure and a weak blockade of adrenergic $\alpha$-receptors.

The above information regarding pharmacological properties is based on the results of appropriate pharmacological experiments in customary test procedures. Thus, the novel $\beta$-blocking compounds exhibit inhibition of tachycardia induced by isoproterenol in the isolated hearts of guinea pigs in a concentration range of from approximately 0.001 $\mu$g/ml to approximately 1 $\mu$g/ml, and in narcotised cats in a dosage range of from approximately 0.001 mg/kg to approximately 10 mg/kg in the case of intravenous administration. The inhibition of vasodilatation induced by isoproterenol in narcotised cats with perfusion of the Arteria femoralis can be detected in dependence on the extent of cardioselectivity in the case of intravenous administration only in higher doses. The ISA of the compounds of the formula I having $\beta$-blocking properties is apparent from the increase in basal heart frequency in narcotised cats treated beforehand with reserpinol, in the case of intravenous administration in a dosage range of from approximately 0.001 mg/kg to approximately 3 mg/kg. In a dosage range of from approximately 0.01 mg/kg to approximately 10 mg/kg in the case of intravenous administration, the novel compounds bring about a reduction in the arterial blood pressure in narcotised cats. The bradycardic action occurs in narcotised cats in dosages of from approximately 0.01 mg/kg to approximately 10 mg/kg and can also be detected in the isolated spontaneously beating right atrium of guinea pigs in a concentration range of from approximately 1 $\mu$g/ml to approximately 30 $\mu$g/ml. The additional $\alpha$-blocking activity is demonstrated, for example, by the antagonisation of noradrenalin-induced contraction of the isolated Vas deferens of rats by such compounds in a concentration range of from 1 $\mu$g/ml to approximately 30 $\mu$g/ml. The novel $\beta$-blocking compounds of the formula I can be used as $\beta$-receptor blockers with or without cardioselectivity and with or without ISA, for example for the treatment of Angina pectoris, hypertrophic cardiomyopathy and heart rhythm disorders and also as blood-pressure-reducing agents. Further possible therapeutic applications are, for example, in the case of increased intraocular pressure and in the case of the thyrotoxicosis.

The compounds of the formula I having $\beta$-receptor-stimulating properties bring about an increase in the heart frequency and myocardial contraction force in the isolated atrium of guinea pigs in a concentration range of from approximately 0.001 $\mu$g/ml to 1 $\mu$g/ml and an increase in the heart frequency in narcotised cats treated beforehand with reserpinol, in a dosage range of from approximately 0.001 mg/kg to approximately 1 mg/kg i.v.. The dosages required to reduce the arterial blood pressure in narcotised cats are, by comparison, higher, corresponding to a dosage range of from approximately 0.01 mg/kg to approximately 10 mg/kg i.v., that is to say, the novel compounds preferentially stimulate the cardiac $\beta$-receptors ($\beta_1$-receptors) in comparison with the $\beta$-receptors in the blood vessles ($\beta_2$-receptors) and, in that respect, differ from isoproterenol which stimulates the $\beta$-receptors of the heart and those of the blood vessels to approximately the same extent. The novel compounds having $\beta$-receptor-stimulating properties can therefore be used as positively inotropically active agents, especially as cardiotonics for the treatment of cardiac muscle insufficiency, on their own or together with other preparations, such as cardiac glycosides.

The compounds of the formula I can also be used as valuable intermediates for the production of other valuable, in particular pharmaceutically active, compounds.

The invention relates especially to compounds of the formula I in which Ar represents an optionally substituted mono- or bi-cyclic carbocyclic aryl radical, or an optionally substituted mono- or bi-cyclic heterocyclic aryl radical that has 5 or 6 ring members, is bonded to the phenylene radical Ph by way of a ring carbon atom and that may be at least partially hydrogenated and, in that case, may be substituted by oxo, the substituents being optionally substituted lower alkyl, for example lower alkyl, hydroxy-lower alkyl, lower alkoxy-lower alkyl, halo-lower alkyl, lower alkanoylamino-lower alkyl, lower alkoxycarbonylamino-lower alkyl, or lower alkenyl, lower alkynyl, optionally etherified or esterified hydroxy or mercapto, for example hydroxy, lower alkoxy, hydroxy-lower alkoxy, phenyl-lower alkoxy, lower alkoxy-lower alkoxy, lower alkylthio-lower alkoxy, halo-lower alkoxy, lower alkanoyl-lower alkoxy, lower alkenyloxy, lower alkynyloxy, lower alkylthio, lower alkylsulphonyl, or halogen, acyl, for example lower alkanoyl, optionally esterified carboxy, such as carboxy or lower alkoxycarbonyl, carbamoyl, N-lower alkylcarbamoyl or N,N-di-lower alkylcarbamoyl, cyano, nitro and/or optionally substituted, such as acylated, amino, for example amino, N-lower alkylamino, N,N-di-lower alkylamino, lower alkanoylamino, lower alkoxycarbonylamino, ureido, 3-lower alkylureido or 3-cycloalkylureido, and, in addition, substituents of heterocyclic aryl Ar being phenyl or benzoyl optionally substituted as stated, or monocyclic heteroaryl optionally substituted as stated, Ph represents 1,3- or 1,4-phenylene optionally substituted as stated, n has the value 0 or 1, and alk represents an alkylene radical having from 2 to 4 carbon atoms, the nitrogen atom and the oxygen atom or, if n is 0, the aromatic radical being separated from each other by 2 or 3 carbon atoms in the unbranched chain, $R_1$ and $R_2$ have the meanings given under formula I, but preferably represent hydrogen or lower alkyl or, together with the nitrogen atom of the amide group, form morpholino or alkyleneamino having 5 or 6 ring members, such as 1-pyrrolidinyl or piperidino, or the N-oxides and salts thereof, especially acid addition salts, more especially pharmaceutically acceptable non-toxic acid addition salts thereof.

The invention relates more especially to compounds of the formula I in which Ar represents an optionally substituted carbocyclic aryl radical, or an optionally substituted heteroaryl radical that has 5 or 6 ring members, is bonded to the phenylene radical Ph by way of a ring carbon atom, contains an oxygen, sulphur or nitrogen atom and, optionally, from 1 to 3 additional nitrogen atoms as ring members and that may be at least partially hydrogenated and, in that case, may be substituted by oxo, and the substituents are optionally substituted lower alkyl, for example lower alkyl, hydroxy-lower alkyl, halo-lower alkyl, or lower alkenyl, optionally etherified or esterified hydroxy or mercapto, for example hydroxy, lower alkoxy, phenyl-lower alkoxy, lower alkoxy-lower alkoxy, halo-lower alkoxy, lower alkenyloxy, lower alkylthio, lower alkylsulphonyl, or halogen, acyl, for example lower alkanoyl, optionally esterified carboxy, such as carboxy or lower alkoxycarbonyl, carbamoyl, N-lower alkylcarbamoyl or N,N-di-lower alkylcarbamoyl, cyano, nitro, optionally substituted, such as acylated, amino, for example amino, N-lower alkylamino, N,N-di-lower alkylamino, lower alkanoylamino, lower alkoxycarbonylamino, or phenyl or benzoyl each optionally substituted by lower alkyl, lower alkoxy, halogen, halo-lower alkyl, nitro or cyano, and/or monocyclic heteroaryl containing an oxygen or nitrogen atom and, optionally, from 1 to 3 further nitrogen atoms and optionally substituted as stated, Ph represents 1,4-phenylene optionally substituted by lower alkyl, lower alkoxy, halo-lower alkyl, halogen or by cyano, n has the value 0 or 1, and alk represents an alkylene radical having from 2 to 4 carbon atoms, the nitrogen atom and the oxygen atom or, if n is 0, the aromatic radical being separated from each other by 2 or 3 carbon atoms in the unbranched chain, $R_1$ and $R_2$ represent hydrogen or lower alkyl or, together with the nitrogen atom of the amide group, form 1-pyrrolidinyl, piperidino or morpholino, or the N-oxides and salts thereof, especially acid addition salts, more especially pharmaceutically acceptable non-toxic acid addition salts thereof.

The invention relates especially to compounds of the formula I in which Ar represents an optionally substituted phenyl radical, or an optionally substituted monocyclic heteroaryl racial that has 5 or 6 ring members, is bonded to the phenylene radical Ph by way of a ring carbon atom, contains an oxygen, sulphur or nitrogen atom and, optionally, from 1 to 3 additional nitrogen atoms as ring members and that may be at least partially hydrogenated and, in that case, may be substituted by oxo, the substituents being optionally substituted lower alkyl, for example lower alkyl, hydroxy-lower alkyl, halo-lower alkyl, or lower alkenyl, optionally etherified or esterified hydroxy, for example hydroxy, lower alkoxy, phenyl-lower alkoxy, halo-lower alkoxy, lower alkenyloxy, lower alkylthio, lower alkylsulphonyl or halogen, acyl, for example lower alkanoyl, optionally esterified carboxy, such as carboxy or lower alkoxycarbonyl, carbamoyl, cyano, nitro, optionally substituted, such as acylated, amino, for example amino, N-lower alkylamino, N,N-di-lower alkylamino, lower alkanoylamino, lower alkoxycarbonylamino, or phenyl or benzoyl each optionally substituted by lower alkyl, lower alkoxy, halogen, halo-lower alkyl, nitro or cyano, and/or monocyclic heteroaryl containing an oxygen or nitrogen atom and, optionally, from 1 to 3 further nitrogen atoms and optionally substituted as stated, Ph represents 1,4-phenylene optionally substituted by lower alkyl, lower alkoxy, halogen or by cyano, n has the value 0 or 1, and alk represents an alkylene radical having from 2 to 4 carbon atoms, the nitrogen atom and the oxygen atom or, if n is 0, the aromatic radical being separated from each other by 2 or 3 carbon atoms in the unbranched chain, $R_1$ and $R_2$ represents hydrogen or lower alkyl or, together with the nitrogen atom of the amide group, form 1-pyrrolidinyl or morpholino, or the N-oxides or salts thereof, especially acid addition salts, more especially pharmaceutically acceptable non-toxic acid addition salts thereof.

The invention relates especially to compounds of the formula I in which Ar represents an optionally substituted phenyl radical, or an optionally substituted monocyclic heteroaryl radical that has 5 or 6 ring members, is bonded to the phenylene radical Ph by way of a ring carbon atom and contains an oxygen, sulphur or nitrogen atom and, optionally, 1 or 2 additional nitrogen atoms as ring members, or represents an at least partially hydrogenated oxoheteroaryl radical having 1 or 2 nitrogen atoms as ring members, the substituents being optionally substituted lower alkyl, for example lower alkyl, hydroxy-lower alkyl, halo-lower alkyl, optionally etherified or esterified hydroxy, for example hydroxy, lower alkoxy, phenyl-lower alkoxy, lower alkylthio, or lower alkylsulphonyl, or halogen, acyl, for example lower alkanoyl, optionally esterified carboxy, such as carboxy or lower alkoxycarbonyl, carbamoyl, cyano, optionally substituted, such as acylated, amino, for example amino, N-lower alkylamino, N,N-di-lower alkylamino, lower alkanoylamino, lower alkoxycarbonylamino, or phenyl or benzoyl each optionally substituted by lower alkyl, lower alkoxy, halogen, halo-lower alkyl or cyano, and/or monocyclic heteroaryl containing an oxygen or nitrogen atom and, optionally, 1 or 2 further nitrogen atoms and optionally substituted as stated, Ph represents 1,4-phenylene optionally substituted by lower alkyl, lower alkoxy, halogen or by cyano, n has the value 0 or 1, and alk represents an alkylene radical having 2 or 3 carbon atoms, the nitrogen atom and the oxygen atom or, if n is 0, the aromatic radical being separated from each other by 2 or 3 carbon atoms in the unbranched chain, $R_1$ and $R_2$ represent hydrogen or lower alkyl or, together with the nitrogen atom of the amide group, form morpholino, or the N-oxides and salts thereof, especially acid addition salts, more especially pharmaceutically acceptable non-toxic acid addition salts thereof.

The invention relates more especially to compounds of the formula I in which Ar represents an optionally substituted phenyl radical, or an optionally substituted heteroaryl radical that has 5 or 6 ring members, is bonded to the phenylene radical Ph by way of a ring carbon atom and contains an oxygen, sulphur or nitrogen atom and, optionally, 1 or 2 additional nitrogen atoms as ring members, for example furyl, oxazolyl, imidazolyl, triazolyl, thiazolyl, indolyl or pyridyl, or represents a dihydro-oxoheteroaryl radical having 1 or 2 nitrogen atoms as ring members, for example dihydro-oxo-2-pyridinyl or dihydro-4-oxo-2-pyrimidinyl, the substituents being lower alkyl, for example methyl, hydroxy-lower alkyl, for example 2-hydroxyethyl, halo-lower alkyl, for example trifluoromethyl, hydroxy, lower alkoxy, for example methoxy, lower alkylthio, for example methylthio, lower alkylsulphonyl, for example methylsulphonyl, halogen, lower alkanoyl, for example acetyl, carboxy, lower alkoxycarbonyl, for example methoxycarbonyl, cyano, carbamoyl, amino, lower alkanoylamino, for example acetylamino, lower alkoxycarbonylamino, for example methoxycarbonylamino, and/or optionally substituted, as stated, heteroaryl, for example imidazolyl, or monocyclic heteroaryl containing an oxygen or nitrogen atom and, optionally, a further nitrogen atom, for example furyl or oxazolyl, Ph represents 1,4-phenylene optionally substituted by lower alkyl, such as methyl, or by halogen, such as chlorine, n has the value 0 or 1, alk represents an alkylene radical having 2 or 3 carbon atoms, the nitrogen atom and the oxygen atom or, if n is 0, the aromatic radical being separated from each other by 2 or 3 carbon atoms in the unbranched chain, and $R_1$ and $R_2$ each represents hydrogen, or the N-oxides and salts thereof, especially acid addition salts, more especially pharmaceutically acceptable non-toxic acid addition salts thereof.

The invention relates specifically to the compounds of the formula I or the N-oxides and salts thereof, especially acid addition salts, more especially pharmaceutically acceptable non-toxic acid addition salts thereof which are mentioned in the Examples.

The novel compounds of the formula I are manufactured in a manner known per se. They can be obtained, for example, as follows: in a compound of the formula

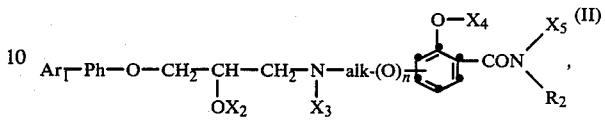

in which $Ar_1$ represents the radical Ar or a radical corresponding thereto having at least one functional grouping in protected form, $X_2$, $X_3$ and $X_4$ each represents hydrogen or a substituent that can be replaced by hydrogen, $X_5$ represents $R_1$ or a substituent that can be replaced by hydrogen, or $X_2$ and $X_3$ and/or $X_4$ and $X_5$ together represent a bivalent radical that can be replaced by two hydrogen atoms, and/or functional groups optionally present in the radical $Ar_1$ are optionally in protected form, with the proviso that at least one of the radicals $X_2$, $X_3$, $X_4$ or $X_5$ is different from hydrogen, or at least $Ar_1$ represents a radical Ar that contains at least one functional grouping in protected form, or at least $X_2$ and $X_3$ together or $X_4$ and $X_5$ together represent a bivalent radical that can be replaced by two hydrogen atoms, or in a salt thereof, the groups $X_2$, $X_3$, $X_4$ or $X_5$, or $X_2$ and $X_3$ together, or $X_4$ and $X_5$ together that are different from hydrogen are replaced by hydrogen atoms, and/or the protecting groups bonded to one or more of the functional groups in a radical $Ar_1$ are split off and replaced by hydrogen, and, if desired, a resulting compound is converted into a different compound of the formula I and/or, if desired, a resulting free compound is converted into a salt or a resulting salt is converted into a free compound and/or, if desired, a resulting mixture of isomers is separated into the isomers or a resulting racemate is resolved into the antipodes.

Protected functional groups in a radical $Ar_1$ are, for example, protected hydroxy, amino or mercapto groups, and, as a ring member in a heteroaryl radical Ar, a protected —NH— group, the protecting groups being groups that can be split off and replaced by hydrogen.

The splitting off of the groups $X_2$, $X_3$ or $X_4$, or $X_2$ and $X_3$ together, or $X_4$ and $X_5$ together and also of the protecting groups present at the functional groups, for example hydroxy and/or amino groups, in a radical $Ar_1$, is carried out by means of solvolysis, such as hydrolysis, alcoholysis or acidolysis, or by means of reduction including hydrogenolysis.

An especially suitable group $X_3$ or $X_4$ that can be split off, or a hydroxy- or amino-protecting group in a radical $Ar_1$ is especially an α-aryl-lower alkyl group that can be split off by hydrogenolysis, such as an optionally substituted 1-polyphenyl-lower alkyl or 1-phenyl-lower alkyl group, for example benzhydryl or trityl, in which the substituents, especially of the phenyl moiety, may be, for example, lower alkyl, such as methyl, or lower alkoxy, such as methoxy, and is especially benzyl. A group $X_3$ and especially $X_2$ and $X_4$ and also hydroxy- and/or amino-protecting groups in a radical Ar may alternatively be a radical that can be split off by solvolysis, such as hydrolysis or acidolysis, or by reduction, including hydrogenolysis, especially a corresponding acyl radical, such as the acyl radical of an organic carboxylic acid, for example lower alkanoyl, such as acetyl, or aroyl, such as benzoyl, or the acyl radical of a semiester of carbonic acid, such as lower alkoxycarbonyl, for example methoxycarbonyl, ethoxycarbonyl or tert.-butoxycarbonyl, 2-halo-lower alkoxycarbonyl, for example 2,2,2-trichloroethoxycarbonyl or 2-iodoethoxycarbonyl, optionally substituted 1-phenyl-lower alkoxycarbonyl, for example benzyloxycarbonyl or diphenylmethoxycarbonyl, or aroylmethoxycarbonyl, for example phenacyloxycarbonyl, or a 1-polyphenyl-lower alkyl group that is optionally substituted, for example as stated above, and is especially trityl.

A radical that can be split off and is formed by $X_2$ and $X_3$ or by $X_4$ and $X_5$ together is especially a group that can be split off by hydrogenolysis, such as optionally substituted 1-phenyl-lower alkylidene, in which the substituents, especially of the phenyl moiety, may be, for example, lower alkyl or lower alkoxy, and is especially benzylidene, or cycloalkylidene, for example cyclopentylidene or cyclohexylidene, and for $X_2$ and $X_3$ together is the carbonyl group.

Starting materials that can be used in the form of salts are used especially in the form of acid addition salts, for example with mineral acids, and also with organic acids.

Radicals $X_2$, $X_3$, $X_4$ and/or $X_5$ that can be split off by hydrogenolysis, especially optionally substituted 1-phenyl-lower alkyl groups, and suitable acyl groups, such as optionally substituted 1-phenyl-lower alkoxycarbonyl, and optionally substituted 1-phenyl-lower alkylidene groups formed by the groups $X_2$ and $X_3$ and also by $X_4$ and $X_5$ together, and hydroxy- and/or amino-protecting groups of that kind present in a radical Ar can be split off by treating with catalytically activated hydrogen, for example with hydrogen in the presence of a catalyst, such as a suitable noble metal catalyst, for example palladium or platinum.

Groups $X_2$, $X_3$, $X_4$ and/or $X_5$ that can be split off by hydrolysis, such as acyl radicals of organic carboxylic acids, for example lower alkanoyl, and of semiesters of carbonic acid, for example lower alkoxycarbonyl, and also, for example, trityl radicals, and lower alkylidene, 1-phenyl-lower alkylidene or cycloalkylidene groups formed by the radicals $X_2$ and $X_3$ and/or $X_4$ and $X_5$ together, and protecting groups of that kind present at functional groups, such as at hydroxy, mercapto or amino groups, in a radical $Ar_1$ and/or at an —NH— group present as a ring member of a heteroaryl radical Ar can be split off, depending on the kind of such radicals, by treating with water under acidic or basic conditions, for example in the presence of a mineral acid, such as hydrochloric or sulphuric acid, or of an alkali metal or alkaline earth metal hydroxide or carbonate or of an amine, such as isopropylamine.

Radicals $X_2$, $X_3$, $X_4$ and/or $X_5$ and/or protecting groups present at functional groups, such as those mentioned, for example at hydroxy, mercapto or amino, in a radical $Ar_1$ which can be split off by acidolysis are especially certain acyl radicals of semiesters of carbonic acid, such as, for example, tert.-lower alkoxycarbonyl or optionally substituted diphenylmethoxycarbonyl radicals, and also the tert.-lower alkyl radical; such radicals can be split off, for example, by treating with suitable strong organic carboxylic acids, such as lower alkanecarboxylic acids optionally substituted by halogen, especially by fluorine, especially with trifluoroacetic acid (if necessary, in the presence of an activating agent, such as anisole), and also with formic acid.

By radicals $X_2$, $X_3$, $X_4$ and/or $X_5$ and/or protecting groups present at functional groups, such as those mentioned, for example at hydroxy and/or amino, in a radical $Ar_1$ which can be split off by reduction there is to be understood also those groups which can be split off by treating with a chemical reducing agent (especially with a reducing metal or a reducing metal compound). Such radicals are especially 2-halo-lower alkoxycarbonyl or arylmethoxycarbonyl, which can be split off, for example, by treating with a reducing heavy metal, such as zinc, or with a reducing heavy metal salt, such as chromium(II) salt, for example chromium(II) chloride or acetate, usually in the presence of an organic carboxylic acid, such as formic acid or acetic acid, and of water.

Protecting groups present at functional groups, for example hydroxy and/or amino groups, in a radical $Ar_1$ correspond to the groups mentioned above that can be split off by the described methods and replaced by hydrogen, such groups being split off in the course of the described process simultaneously with other groups or subsequently in a separate process step.

The above reactions are usually carried out in the presence of a solvent or solvent mixture, it being possible for suitable reactants to function simultaneously as such, and, if necessary, while cooling or heating, for example in an open or closed vessel and/or in the atmosphere of an inert gas, for example nitrogen.

The starting materials of the formula II can be obtained, for example, by reacting a compound of the formula

$$Ar_1\text{—Ph—OH} \qquad (IIa),$$

or a salt thereof, with a compound of the formula

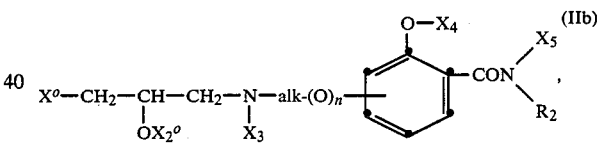

in which X° represents a reactive esterified hydroxy group and $X_2°$ represents the group $X_2$, or X° and $X_2°$ represent the direct bond, and $Ar_1$ and the other groups have the meanings given above, or by treating a compound of the formula

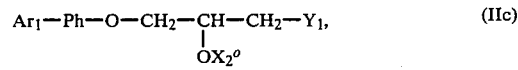

$$Ar_1\text{—Ph—O—CH}_2\text{—CH—CH}_2\text{—Y}_1, \qquad (IIc)$$
$$\qquad\qquad\qquad\quad |$$
$$\qquad\qquad\qquad\;\; OX_2°$$

with a compound of the formula

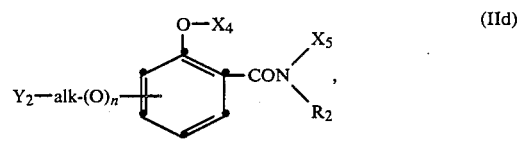

in which $X_2°$ has the meaning given above for $X_2$ and one of the groups $Y_1$ and $Y_2$ represents a reactive esterified hydroxy group, for example halogen, such as chlorine or bromine, and the other represents a group of the formula —NH($X_3$), or in which $X_2°$ and $Y_1$ represent the direct bond and $Y_2$ represents a group of the formula —NH(X₃), wherein X₃ has in each case the meaning given above. The above reactions are carried out in a manner known per se.

If, for example, Y₁ or Y₂ represents a reactive esterified hydroxy group, for example chlorine, the reaction is carried out in the presence of a basic agent, for example an alkali metal or alkaline earth metal carbonate, such as potassium or calcium carbonate, or an alkali metal or alkaline earth metal hydroxide, such as sodium or calcium hydroxide, advantageously in the presence of a suitable solvent, such as a lower alkanol, for example ethanol, or an alkanone, for example acetone.

Furthermore, the Schiff's base formed, for example, by reacting a compound of the formula

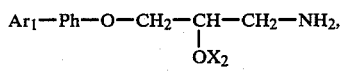  (IIe)

with a carbonyl compound of the formula

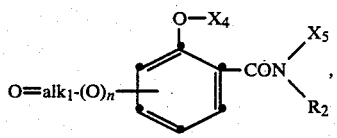  (IIf)

in which alk₁ represents an alkylidene radical corresponding to the radical alk and at least one of the radicals X₂, X₄ or X₄ and X₅ together represents one of the mentioned protecting groups, or at least Ar₁ represents a radical Ar in which at least one functional grouping is in protected form, can be reduced to a compound of the formula II with a reducing agent, for example a borohydride, such as sodium borohydride. The reduction can also be effected by means of activated hydrogen, for example hydrogen in the presence of a hydrogenation catalyst, for example a platinum-on-carbon catalyst.

Carbonyl compounds of the formula (IIf) in which n is 1 can, in their turn, be obtained in customary manner by reacting a compound of the formula

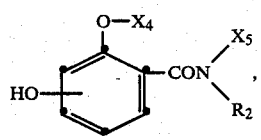  (IIg)

or a salt thereof, with a compound of the formula (O=alk₁)-Hal (IIh) in which alk₁ has the meaning given above and Hal represents halogen, and such compound is, for example, a haloketone, such as chloroacetone.

Phenols of the formula IIa can, in their turn, be obtained by forming the mono- or bi-cyclic heteroaryl group Ar₁ in a compound of the formula

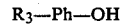 R₃—Ph—OH  (IIi), in which R₃ represents a substituent optionally containing protecting groups and capable of forming a mono- or bi-cyclic heteroaryl radical Ar₁, and the phenolic hydroxy group is optionally in protected form, for example in etherified form, for example as methoxy, in esterified form, for example as acetoxy, or in silylated form, for example as trimethylsilyloxy, and by simultaneously or subsequently splitting off optionally present protecting groups and replacing them by hydrogen.

Thus, compounds of the formula IIa, in which Ar has the meaning given and represents, for example, an imidazolyl, benzimidazolyl, pyrrolyl, indolyl, pyrazolyl, thiazolyl, thiadiazolyl, pyrimidinyl or triazolyl radical, can be obtained in customary manner from a compound of the formula IIi analogously to the methods described for the formation of a corresponding heteroaryl radical Ar in a compound of the formula VIII.

The novel compounds of the formula I can also be obtained by reacting a compound of the formula

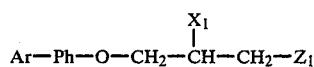  (III)

with a compound of the formula

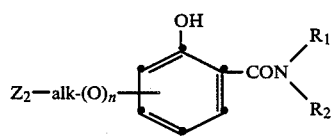  (IV)

or with a salt thereof, in which one of the groups Z₁ and Z₂ represents a reactive esterified hydroxy group and the other represents a primary amino group and X₁ represents hydroxy, or in which X₁ and Z₁ together represent the epoxy group and Z₂ represents a primary amino group and Ar, Ph, n, alk, R₁ and R₂ have the meanings given above, and, if desired, carrying out the additional process steps.

A reactive esterified hydroxy group Z₁ or Z₂ is a hydroxy group esterified by a strong acid, especially a strong inorganic acid, such as a hydrohalic acid, especially hydrochloric, hydrobromic or hydriodic acid, or sulphuric acid, or a strong organic sulphonic acid, such as an aliphatic or aromatic sulphonic acid, for example methanesulphonic acid, 4-methylphenylsulphonic acid or 4-bromophenylsulphonic acid, and is especially halogen, for example chlorine, bromine or iodine, or aliphatically or aromatically substituted sulphonyloxy, for example methylsulphonyloxy or 4-methylphenylsulphonyloxy.

The above-described reaction is carried out in a manner known per se and, especially when using a starting material having a reactive esterified hydroxy group, advantageously in the presence of a basic agent, such as an inorganic base, for example an alkali metal or alkaline earth metal carbonate or hydroxide, or an organic basic agent, such as an alkali metal lower alkoxide, and/or an excess of the basic reactant and usually in the presence of a solvent or solvent mixture and, if necessary, while cooling or heating, for example within a temperature range of from approximately −20° C. to approximately +150° C., in an open or closed vessel and/or in an inert gas atmosphere, for example in a nitrogen atmosphere.

Starting materials of the formula III are known or can be manufactured in a manner known per se. They can thus be obtained, for example, by reacting a phenol of the formula

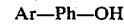 Ar—Ph—OH  (IIIa)

or a salt thereof, with a compound of the formula

(IIIb)

in which X° represents a suitable leaving group, for example a reactive esterified hydroxy group, such as halogen, for example chlorine, and preferably $X_1$ and $Z_1$ together represent epoxy.

Phenols of the formula IIIa can, in their turn, be obtained in customary manner, for example in a manner analogous to that of the manufacture of phenols of the formula IIa described above.

Starting materials of the formula IV in which $Z_2$ represents halogen and n has the value 1 can be manufactured, for example, by reacting a hydroxysalicylamide with a dihaloalkane corresponding to the meaning of alk, for example a chlorobromoalkane or dibromoalkane, in the presence of an alkaline condensation agent, such as an alkali metal carbonate. From this, a starting material of the formula III in which $Z_2$ is primary amino can be obtained, for example, by reacting with hexamethylenetetramine and decomposing the resulting adduct with an aqueous mineral acid, for example dilute hydrochloric acid. These reactions are carried out in customary manner.

Starting materials of the formula IV in which $Z_2$ represents halogen and n has the value 0, can be obtained, in a manner known per se, for example by reacting a phenol of the formula

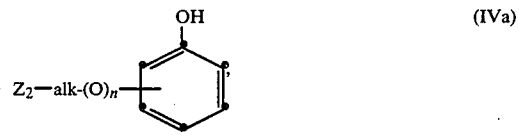

(IVa)

or an alkali metal salt, for example the sodium salt, with carbon dioxide under the conditions of a Kolbe synthesis to form correspondingly substituted salicylic acid, and by converting the latter, for example by way of the acid chloride obtainable in customary manner by means of thionyl chloride, into the substituted salicylamide corresponding to the radicals $R_1$ and $R_2$.

The novel compounds can also be obtained by reducing $X_6$ in a compound of the formula

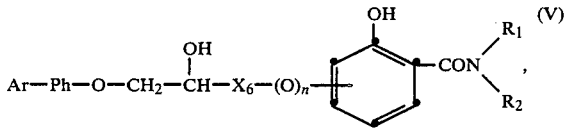

(V)

in which $X_6$ represents a reducible group of the formula

—CH=N—alk—(Va) or —CH$_2$—N=alk$_1$— (Vb)

wherein alk$_1$ represents an alkylylidene radical corresponding to the radical alk and n has the value 0 or 1, to the group of the formula —CH$_2$—NH—alk— (Vc)

simultaneously or subsequently splitting off optionally present protecting groups which are located at functional groups and do not participate in the reaction and replacing them by hydrogen and, if desired, carrying out the additional process steps. Protecting groups of protected functional groups, for example those of the kind mentioned above, such as protected hydroxy and/or amino groups, are especially groups that can be split off by hydrogenolysis, for example an α-aryl-lower alkyl group, such as an optionally substituted 1-phenyl-lower alkyl group, in which the substituents, for example of the phenyl radical, may be, for example, lower alkoxy, such as methoxy, and especially benzyl, such protecting groups being split off in the course of the described process simultaneously or subsequently in a separate process step.

Starting materials of the formula V having a group $X_6$ of the formula Vb may also be in the isomeric form of ring tautomers of the formula

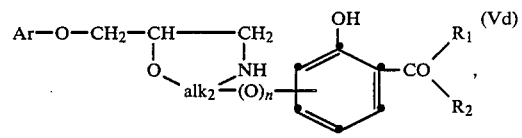

(Vd)

in which alk$_2$ corresponds to the meaning of alk$_1$ or represents an alkylidene group, and the oxygen and nitrogen atoms of the ring are bonded to the same carbon atom.

An alkyl-ylidene group alk is, for example, methine or ethylylidene, whilst an alkylidene group alk$_2$ is, for example, methylene, ethylidene or 1-methyl-ethylidene.

The reduction of the nitrogen-carbon double bond in starting materials of the formula V which contain, as $X_6$, a group Va or Vb, to a nitrogen-carbon single bond of the group Vc can be carried out in a manner known per se, for example by treating with catalytically activated hydrogen, such as hydrogen in the presence of a suitable hydrogenation catalyst, for example a nickel, platinum or palladium catalyst, protecting groups that can be split off by hydrogenolysis being split off at the same time and replaced by hydrogen; or reduction is carried out with a suitable hydride reducing agent, such as an alkali metal borohydride, for example sodium borohydride. When using a hydride reducing agent, acyl radicals of carboxylic acids, for example acetic acid, that are bonded to oxygen as protecting groups can be split off in the same step.

A starting material of the formula V can be produced in a manner known per se, optionally in situ, i.e. under the conditions of the described process. Thus, a compound of the formula

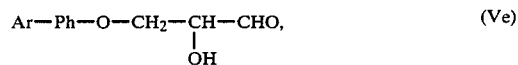

(Ve)

can be reacted with an amine of the formula

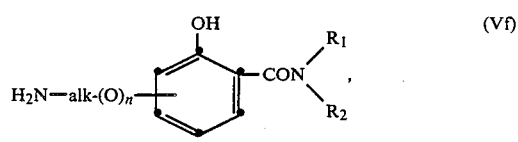

(Vf)

functional groups, for example hydroxy groups, optionally being in protected form, for example as described, to form a starting material of the formula V having the group $X_6$ of the formula Va.

By reacting a compound of the formula

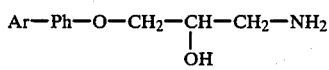

with a carbonyl compound of the formula

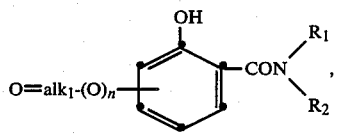

in which alk₁ has the meaning given under formula IIf and functional groups, for example hydroxy groups, not participating in the reaction are optionally in protected form, for example as described, starting materials of the formula V can be obtained.

Oxo compounds of the formula Vi in which n has the value 1 can, in their turn, be obtained, for example, by reacting a compound of the formula

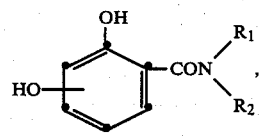

or a salt thereof, with a halo-alkanone compound of the formula IIh described above, for example chloroacetone, in the presence of an alkaline condensation agent, such as potassium carbonate, or an organic base, such as triethylamine.

Amines of the formula Vh can, in their turn, be obtained in customary manner, for example by reacting a compound of the formula

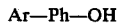

or a salt thereof, with epichlorohydrin to form a compound of the formula

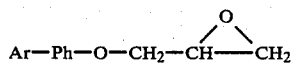

and by reacting the latter with ammonia. Phenols of the formula Vl can, in their turn, be obtained in a manner known per se, corresponding to that of the manufacture of starting materials of the formula IIa, for example as described.

The novel compounds of the formula I can also be obtained by reacting a compound of the formula

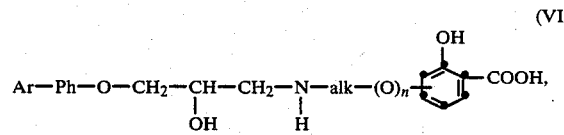

or a reactive derivative of such a carboxylic acid, in which functional groups not participating in the reaction are optionally protected by protecting groups that can be split off by aminolysis or ammonolysis and replaced by hydrogen, with a compound of the formula

and simultaneously or subsequently splitting off optionally present protecting groups and replacing them by hydrogen and, if desired, carrying out the additional process steps.

Protecting groups of protected functional groups, for example those of the kind mentioned, such as protecting groups present at hydroxy and/or amino groups, are radicals that can be split off by aminolysis and especially by ammonolysis, for example acyl radicals of organic carboxylic acids, for example aroyl, such as benzoyl, or lower alkanoyl, such as acetyl.

Reactive derivatives of the carboxylic acids defined in formula VI are, for example, the halides, such as the chlorides or bromides, the azides or the acid anhydrides, especially mixed acid anhydrides, with, for example, lower alkanecarboxylic acids, such as acetic acid or propionic acid, lower alkoxyalkanecarboxylic acids, such as 2-methoxyacetic acid. Reactive derivatives of carboxylic acids of the formula VI are especially esters, for example lower alkyl esters, such as methyl or tert.-butyl esters, also with aryl-lower alkanols, such as benzyl alcohol optionally substituted by lower alkyl, for example methyl or by lower alkoxy, for example methoxy, or phenols that are optionally activated by suitable substituents, for example by halogen, such as 4-halogen, for example 4-chloro, lower alkoxy, for example 4-lower alkoxy, such as 4-methoxy, or 4-nitro or 2,4-dinitro, such as, for example, 4-chlorophenol, 2,3,4,5,6-pentachlorophenol, 4-methoxyphenol, 4-nitro- or 2,4-dinitrophenol, also with cycloalkanols, such as cyclopentanol or cyclohexanol, which may optionally be substituted by lower alkyl, for example methyl. The reaction is carried out in a manner known per se, usually in the presence of an inert solvent, and within a temperature range of approximately from −10° to +150° in a closed vessel.

The starting materials of the formula VI can be obtained in a manner known per se by reacting a compound of the formula (III) in which X₁ and Z₁ together represent an epoxy group, with an amino compound of the formula

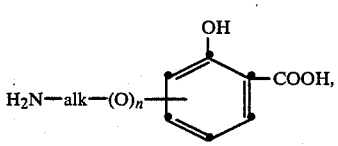

or a reactive derivative of such a carboxylic acid, for example as described under formula VI.

The Schiff's base formed by the reaction of a compound of the formula Vh described above with a carbonyl compound of the formula

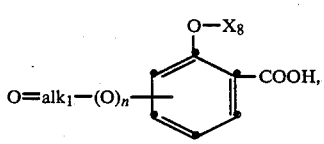

or a reactive carboxylic acid derivative thereof, for example as described under formula VI, in which alk₁ has the meaning given under formula IIf, can also be reduced with a borohydride, for example sodium borohydride. The reduction can also be effected by means of activated hydrogen in the presence of a hydrogenation catalyst, for example a platinum-on-carbon catalyst.

Carbonyl compounds of the formula (VIc) in which n has the value 1 can, in thier turn, be obtained by reacting a compound of the formula

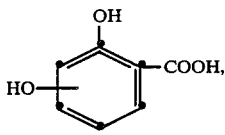

(VId)

or a reactive carboxylic acid derivative thereof, for example as described under formula VI, with a compound of the above-described formula IIH, for example chloroacetone, in the presence of an alkaline agent, for example potassium carbonate, or an organic base, such as triethylamine. During these reactions, functional groups, for example hydroxy groups, not participating in the reaction are optionally in protected form, for example as described. These reactions are carried out in a manner known per se.

The novel compounds of the formula I can also be obtained by converting the group —CN in a compound of the formula

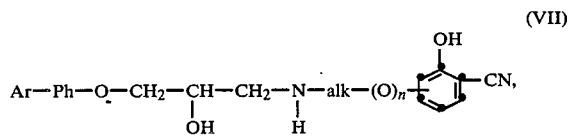

(VII)

in which functional groups not participating in the reaction are optionally protected by protecting groups that can be split off by hydrolysis and replaced by hydrogen and which are split off and replaced by hydrogen under the conditions of the process, into the group —CONH$_2$ by means of hydrolysis and, at the same time, splitting off optionally present protecting groups and replacing them by hydrogen and, if desired, carrying out the additional process steps.

The above reactions are carried out in a manner known per se. Hydrolysis is carried out in a basic or, advantageously, in an acidic medium, espeically in the presence of a concentrated aqueous mineral acid, such as, for example, concentrated hydrochloric acid and, if necessary, while cooling or heating, for example within a temperature range of approximately from 0° to 60°, preferably approximately 40° to 50°, in an open or closed vessel and/or in an inert gas atmosphere, for example in a nitrogen atmosphere.

The starting materials of the formula VII can be manufactured, for example, by reacting a compound of the formula III described above with a compound of the formula

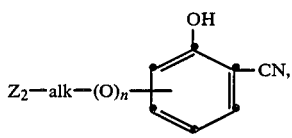

(VIIa)

in which one of the groups $Z_1$ and $Z_2$ represents a reactive esterified hydroxy group and the other represents a primary amino group, and $X_1$ represents hydroxy, or in which $X_1$ and $Z_1$ together represent an epoxy group and $Z_2$ represents a primary amino group, and Ar, Ph, n, alk, $R_1$ and $R_2$ have the meanings given above. Reactive esterified hydroxy groups $Z_1$ or $Z_2$ are preferably halogen, especially chlorine, bromine or iodine. If $Z_1$ or $Z_2$ represents a reactive esterified hydroxy group, the reaction is advantageously carried out in a manner known per se in the presence of a basic agent.

The compound VIIa can, in its turn, be produced by the action of acetic anhydride on the oxime corresponding to the cyanide. Advantageously, this is achieved by boiling under reflux. The oxime can, for its part, be produced from the corresponding aldehyde by boiling under relux with hydroxylamine hydrochloride in the presence of a alcoholic soda solution. The corresponding aldehyde can in turn be manufactured by reacting 2,4-dihydroxybenzaldehyde with an $\alpha,\omega$-dihalo-lower alkane, preferably in the presence of a basic agent. Alternatively, a hydroxysalicylonitrile, for example 2,4-dihydroxybenzonitrile [Chem. Ber. 24, 3657 (1891)] or 2,5-dihydroxybenzonitrile [Helv. Chim. Acta 30, 149, 153(1947)], can be reacted in an analogous manner with a non-geminal dihalo-lower alkane to form a compound of the formula VIIa.

The novel compounds of the formula I in which Ar represents a mono- or bi-cyclic heteroaryl radical can also be obtained by forming the mono- or bi-cyclic heteroaryl group Ar in a compound of the formula

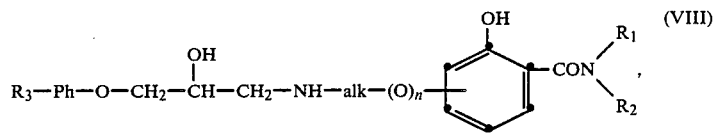

(VIII)

in which hydroxy groups and/or the amino groups are/is protected by protecting groups and $R_3$ represents a substituent capable of forming a mono- or bi-cyclic heteroaryl radical Ar, simultaneously or subsequently splitting off optionally present protecting groups and replacing them by hydrogen and, if desired, carrying out the additional process steps mentioned above. Protecting groups are, for example, acyl, such as lower alkanoyl, such as acetyl, that can be split off and replaced by hydrogen under the process conditions used for the formation of the heteroaryl radical Ar.

Thus, for the manufacture of a compound of the formula I in which Ar represents an imidazolyl radical that is substituted, for example in the 2-position, by the substituted Ph group, a compound of the formula VIII in which $R_3$ represents a formyl group can be reacted in customary manner with a 1,2-dicarbonyl compound of the formula

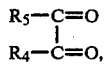  (VIIIa)

in which $R_4$ and/or $R_5$ each represents hydrogen or a radical substituting the heteroaryl group, for example as described above, in the presence of ammonia, or with a monooximino compound corresponding to the formula VIIIa. Depending on the type of radical $R_4$ and/or $R_5$, the compound of the formula VIIIa can be used as such or can be formed in situ in the reaction mixture from a suitable preliminary stage. Preliminary stages suitable for this purpose are, for example, acyloins derived from hydroxyacetone, for example 1-lower alkanoyloxyacetone, such as 1-acetoxyacetone, or 1,1-dihaloacetone, such as, for example, 1,1-dibromoacetone, which is optionally substituted in the 1- and/or 3-position by the group $R_4$ and/or $R_5$. Other preliminary stages are those in which the carbonyl compound of the formula VIIIa is in modified form, for example as an acetal, such as dimethyl acetal, as a hydrate or as a bisulphite addition compound. The compound of the formula VIIIa can be obtained in situ from such preliminary stages as follows: in the presence of a copper(II) salt, for example copper-(II) acetate in the case of acyloins, such as the mentioned 1-acetoxyacetone, or by treatment with hydrolysing agents, preferably weak alkalis, for example sodium acetate in the case of the 1,1-dihaloacetone derivatives, or with aqueous acids in the case of the acetals or bisulphite addition compounds. In this manner, compounds of the formula I are obtained in which the substituted Ph group substituted a 2-position, and a group $R_4$ and/or $R_5$ respectively substitutes the 4- and 5-position, of the imidazole radical formed.

Compounds of the formula I in which the imidazole radical Ar is substituted, for example in the 4-position, by the substituted Ph group, can be obtained, for example, by reacting a compound of the formula VIII in which $R_3$ represents the group

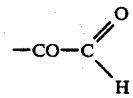  (VIIIb)

with a compound of the formula

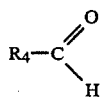  (VIIIc)

and ammonia. In this reaction, the groups of the formula VIIIb or VIIIc may also be in functionally modified form, for example as acetals, such as dimethyl acetals, as hydrates or as bisulphite addition compounds, from which, by treatment with aqueous acids, the free compounds are formed in situ and are then further reacted in the same reaction mixture. These reactions are carried out in customary manner, for example in the presence of a solvent or solvent mixture and, if necessary, while cooling or heating, for example within a temperature range of from approximately $-30°$ to approximately $+150°$ C., if necessary in a closed vessel and/or in an inert gas atmosphere, for example under nitrogen.

The starting materials can be manufactured in a manner known per se.

Thus compounds of the formula VIII in which $R_3$ represents a formyl group or the group of the formula VIIIb can be obtained by reacting a compound of the formula $R_3$—Ph—OH (VIIId) in which the formyl group corresponding to the radical $R_3$, or the group of the formula VIIIb is preferably in protected form, for example as an acetal, such as dimethyl acetal, as a hydrate or as a bisulphite addition compound, for example that formed with sodium sulphite, with epichlorohydrin to form the corresponding 2,3-epoxypropoxy compound and by further reacting the latter with a compound of the formula

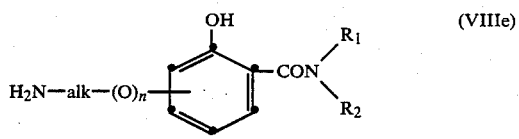  (VIIIe)

for example with 5-(2-aminoethoxy)-salicylamide. An intermediate, for example a Schiff's base, formed in this reaction from the formyl group or the group of the formula VIIIb and a compound of the formula VIIIe is subsequently hydrolysed, for example with acidic agents, such as a mineral acid, for example aqueous hydrochloric acid, whereupon the compound of the formula VIII is obtained.

Instead of the described reaction, a compound of the formula VIIId in which the group $R_3$ represents a formyl group or the group of the formula VIIIb and is preferably in protected form, for example in acetal form, or a salt thereof, for example an alkali metal or alkaline earth metal salt, for example a sodium or calcium salt, can be reacted with an optionally reactive esterified oxazolidine compound of the formula

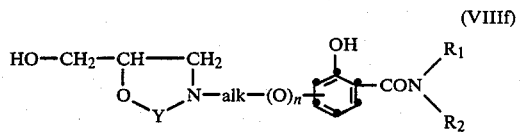  (VIIIf)

in which Y represents a group of the formula

  (VIIIg)

wherein $R_6$ and $R_7$ each represents hydrogen, or the group of the formula VIIIg represents optionally substituted 1-phenyl-lower alkylidene, wherein substituents, especially of the phenyl moiety, may be, for example, lower alkyl or lower alkoxy, and represents especially benzylidene or cycloalkylidene, for example cyclopentylidene or cyclohexylidene, or the group Y represents the carbonyl group

  (VIIIh)

and the resulting compound of the formula

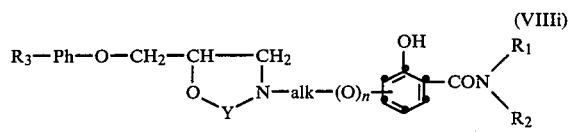  (VIIIi)

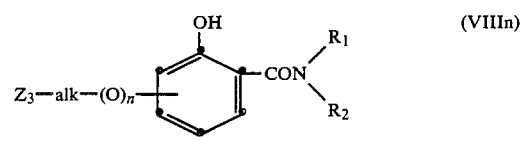  (VIIIn)

can be hydrolysed. A reactive esterified compound of the formula VIIIf is one in which the primary alcohol group is esterified with a suitable acid, for example as described, such as a hydrohalic acid, for example hydrochloric acid, or a strong organic sulphonic acid, such as, for example, p-toluenesulphonic acid. Hydrolysis of a compound of the formula VIIIi is carried out by means of water optionally in the presence of acidically active agents, for example a mineral acid, such as hydrochloric acid or sulphuric acid, acid hydrolysis being used especially in the case of compounds of the formula VIIIi having a group of the formula VIIIg, whilst, at the same time, optionally present protecting groups may be split off and replaced by hydrogen. Compounds of the formula VIIIi having a group Y of the formula VIIIh are advantageously hydrolysed in the presence of alkaline substances, for example strong bases, such as alkali metal hydroxides, for example sodium hydroxide, and it may be advantageous to use in this operation a solvent having a relatively high boiling point, for example butanol. Optionally present protecting groups can be split off simultaneously or subsequently in an acidic medium, for example as described.

These reactions are carried out in a manner known per se.

Compounds of the formula VIIIf in which Y represents the radical of the formula VIIIg can, in their turn, be obtained in customary manner from a compound of the formula

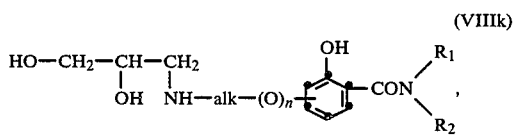  (VIIIk)

by reaction with an oxo compound of the formula

  (VIIIl)

such as, for example, formaldehyde or benzaldehyde, or reactive derivatives thereof, for example the acetals, such as the dimethyl acetals, whilst compounds of the formula VIIIf in which Y represents a radical of the formula VIIIh can be produced in known manner by the action of phosgene on a compound of the formula VIIIk in which the primary hydroxy group is in reactive esterified form.

Finally, starting materials of the formula VIIIf can be obtained by reacting a compound of the formula

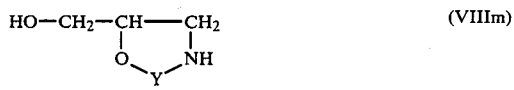  (VIIIm)

with a compound of the formula in which $Z_3$ represents a reactive esterified hydroxy group, for example as defined above, for example halogen, such as chlorine or bromine, in customary manner, preferably in the presence of an alkaline condensation agent, for example potassium carbonate, and in the absence of water, optionally present protecting groups being simultaneously or subsequently split off and replaced by hydrogen.

A compound of the formula I in which Ar represents the thiazolyl radical which is substituted, for example in the 2-position, by the substituted Ph group can be obtained, for example, by reacting a compound of the formula VIII in which $R_3$ represents the group of the formula

  (IXa)

with a compound of the formula

  (IXb)

in which Hal represents halogen, for example chlorine and especially bromine, and $R_4$ and/or $R_5$ each represents hydrogen or a radical substituting the heteroaryl group, for example as described above. Depending on the kind of radical $R_4$ and/or $R_5$, a compound of the formula IXb can be used in the form of its derivatives, for example the acetals, such as the diethyl acetals, or the $\alpha,\beta$-dihaloethyl ethers, such as $\alpha,\beta$-dibromoethyl ethers, for example $\alpha,\beta$-dibromoethylmethyl ether, or the $\alpha,\beta$-dihaloethyl acetates, such as $\alpha,\beta$-dichloroethyl acetates. Instead of a carbonyl compound of the formula IXb, an epoxide of the formula

  (IXc)

in which Hal represents halogen, for example chlorine, can be used for the described reaction.

For the manufacture of compounds of the formula I in which Ar represents a thiazolyl radical substituted in the 4- or 5-position by the substituted Ph group, a compound of the formula VIII in which $R_3$ represents a group of the formula

  (IXd)

or of the formula

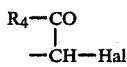 (IXe)

and the carbonyl group is optionally in protected form, for example acetal form, in which Hal represents in each case halogen, for example chlorine or bromine, and R₄ and R₅ have the meanings given above, can be reacted with a compound of the formula

 (IXf)

These reactions are carried out in a manner known per se, for example in the presence of a suitable solvent, for example a lower alkanol, such as ethanol, or an ethereal liquid, such as dioxan, optionally at elevated temperature and optionally in the presence of a basic agent, for example a metal salt, such as an alkali metal or alkaline earth metal salt, of a weak acid, such as carbonic acid or acetic acid, for example magnesium carbonate or sodium acetate, and, if necessary, in a closed vessel and/or in an inert gas atmosphere, for example under nitrogen.

The starting materials can be manufactured according to known methods. Thus, a compound of the formula VIII having the group IXa as R₃ can be obtained by converting the group N≡C— in a compound of the formula

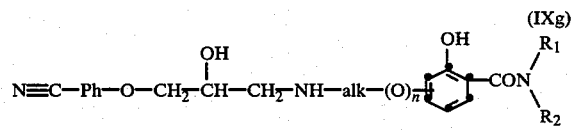 (IXg)

into the group IXa by reacting with hydrogen sulphide in a suitable, for example a basic organic, solvent, such as, for example, pyridine or triethylamine or mixtures thereof.

Starting materials of the formula IXg can, in their turn, be obtained by reacting a compound of the formula

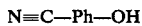
N≡C—Ph—OH (IXh)

with epichlorohydrin to form the corresponding 2,3-epoxypropoxy compound and manufacturing a compound of the formula IXg from that compound by reaction with a compound of the formula VIIIe described above, for example with 5-(2-aminoethoxy)-salicylamide.

Starting materials of the formula VIII in which R₃ represents a group of the formula IXd or IXe can be obtained, for example, by reacting a phenol of the formula

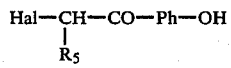 (IXi)

or of the formula

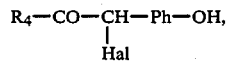 (IXk)

in which Hal represents halogen and especially chlorine or bromine, with a compound of the formula

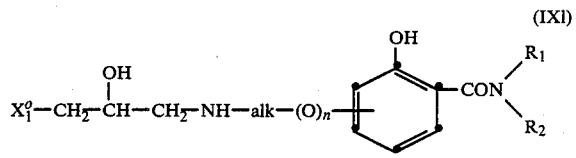 (IXl)

or a corresponding oxazolidine or oxazolidinone compound of the formula

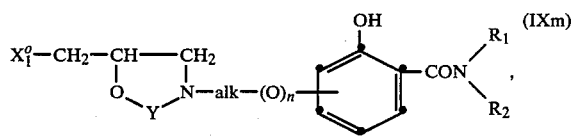 (IXm)

in which Y has the meaning given under the formula VIIIf, and X₁° represents a suitable leaving group, such as a halogen, for example chlorine or especially bromine, or a sulphonyloxy radical, for example the p-tosyloxy radical, and a compound of the formula IXl is, for example, 5-(2-bromoethoxy)-salicylamide. The reaction is advantageously carried out in the presence of a basic agent, such as an inorganic base, for example an alkali metal or alkaline earth metal hydroxide or carbonate, or an organic basic agent, such as an alkali metal lower alkoxide, such as sodium methoxide, and usually in the presence of a solvent or solvent mixture. Polar solvents are advantageously used, for example a lower alkanol, such as ethanol, or an optionally N-lower alkylated fatty acid amide, such as dimethylformamide or N-methylacetamide, dimethyl sulphoxide or sulpholane or mixtures of such solvents.

If a compound of the formula IXm is used for the reaction, this will be followed by the conversion of the resulting compound into a starting material of the formula VIII having the group IXd or IXe as R₃, by subjecting the reaction product to hydrolysis. This is carried out in customary manner by means of water, optionally with the addition of acidically reacting substances, such as a mineral acid, for example hydrochloric acid, or a base, such as, for example, an alkali metal or alkaline earth metal hydroxide. Starting materials of the formula IXl can, in their turn, be obtained, for example, by reacting a compound of the formula VIIIe with epichlorohydrin in customary manner, for example in a solvent, such as a lower alkanol, whereas a compound of the formula IXm can be obtained by reacting a compound of the formula VIIIn described above with a compound of the formula

 (IXn)

These reactions are carried out in customary manner, for example in a suitable solvent, such as a lower alkanol, or a strongly polar non-aqueous solvent, such as an optionally lower alkylated fatty acid amide, such as dimethylformamide, N-methyl- or N,N-dimethylacetamide, also dimethyl sulphoxide, sulpholane or N,N,N',N'-tetramethylurea, advantageously in the presence of a basic agent, such as an alkali metal hydroxide, such as sodium hydroxide, or sodium hydride.

A compound of the formula I in which Ar represents a pyrimidinyl radical which is substituted, for example in the 4(6)-position, by the substituted Ph group can be obtained by reacting, for example, a compound of the formula VIII in which $R_3$ represents a group of the formula

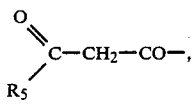 (Xa)

in which the carbonyl group(s) is (are) optionally in protected form, for example acetalised form, for example as dimethyl acetal, or as a bisulphite addition compound, for example with sodium bisulphite, with a compound of the formula

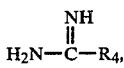 (Xb)

in which $R_4$ and $R_5$ have the meanings given above.

These reactions are carried out in customary manner and preferably under acidic conditions, for example in the presence of an acidically reacting agent, such as, for example, ammonium chloride.

The starting materials can be obtained according to methods known per se.

Thus, for example, a starting material of the formula VIII having the group Xa as $R_3$ can be manufactured by reacting a compound of the formula

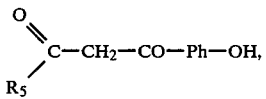 (Xc)

having a preferably protected, for example as described, acetalised carboxaldehyde group, with epichlorohydrin in the presence of a base, for example an organic amine, for example pyridine or collidine, to form a corresponding compound of the formula

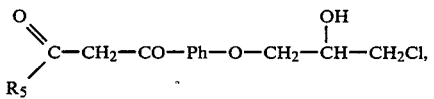 (Xd)

and converting the adduct obtained therefrom by reaction with hexamethylenetetramine in customary manner, into a corresponding compound of the formula

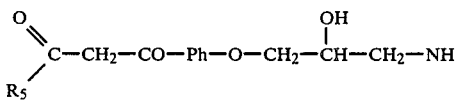 (Xe)

by decomposition with an aqueous mineral acid, for example dilute sulphuric acid, which compound is subsequently reacted with a compound of the formula VIIIn described above, in an analogous manner, for example as described in connection with formula VIIIn, and, after conversion of the optionally protected carboxaldehyde group into the free carboxaldehyde group, for example by means of an acidic agent, such as an aqueous mineral acid, for example dilute sulphuric acid, results in a starting material of the formula VIII having the group Xa as $R_3$. These reactions are carried out in a manner known per se.

For the manufacture of compounds of the formula I in which Ar represents a pyrimidinyl radical which is substituted, for example in the 2-position, by the substituted Ph group, for example a compound of the formula VIII in which $R_3$ represents a group of the formula

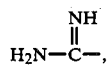 (Xf)

can be reacted with a compound of the formula $$R_4-CO-CH_2-CO-R_5 \qquad (Xg)$$

in which the carbonyl group(s) is (are) optionally in protected, for example acetalised, form, for example as dimethyl acetals, and $R_4$ and $R_5$ have the meanings given above. This reaction is carried out in a manner known per se, for example under acidic conditions, for example as described, for example in the presence of ammonium chloride.

The starting materials can be manufactured according to methods known per se. Thus, for example, a compound of the formula VIII having the group Xf as $R_3$ can be obtained, for example by converting a compound of the above-described formula (IXg) into the corresponding imido esters, for example by saturating an absolute ethanol solution of such a compound with hydrogen chloride, and producing from this, by reaction with anhydrous ammonia, a compound of the formula VIII containing the group Xf as $R_3$, preferably in the form of a salt, for example with a strong acid, for example as the hydrochloride, and by simultaneously or subsequently removing optionally present protecting groups and replacing them by hydrogen.

When selecting a suitable process from those mentioned above for the manufacture of compounds of the formula I, it must be ensured that any substituents present, especially of the radicals Ar, are not converted or split off if such conversions or splitting-off operations are not desired. Thus, in particular, functionally modified carboxy groups, such as esterified or amidated carboxy groups, and cyano groups, present as substituents of the radicals Ar, may participate in the reaction and be converted during solvolyses, especially hydrolyses, and during reductions. On the other hand, simultaneous conversions of substituents may be desired: for example, unsaturated substituents, such as lower alkenyl, may be reduced under the conditions of the reduction process used according to the invention, for example to lower alkyl.

In resulting compounds, it is possible within the scope of the definition of the compounds of the formula I to convert compounds obtained in accordance with the process in customary manner into other end products, for example by modifying, introducing or splitting off suitable substituents.

Free carboxy groups in the radicals Ar can be esterified in customary manner, for example by reacting with a corresponding alcohol, advantageously in the presence of an acid, such as a mineral acid, for example sulphuric acid or hydrochloric acid, or in the presence of a water-binding agent, such as dicyclohexylcarbodiimide, or by reacting with a corresponding diazo compound, for example diazomethane. Esterification can also be carried out by reacting a salt, preferably an alkali metal salt, of the acid with a reactive esterified alcohol, for example a corresponding halide, such as chloride.

Free carboxy groups can be amidated in customary manner, for example by reacting with ammonia or with a primary or secondary amine, advantageously in the presence of a water-binding agent, such as dicyclohexylcarbodiimide, or by converting the carboxy group into a halocarbonyl group, for example a chlorocarbonyl group, and then reacting with ammonia or a primary or secondary amine.

In compounds that contain an esterified carboxy group, the latter can be converted into a free carboxy group in customary manner, for example by hydrolysis, preferably in the presence of strong bases, such as an alkali metal hydroxide, for example sodium or potassium hydroxide, or strong acids, for example a strong mineral acid, such as a hydrohalic acid, for example hydrochloric acid, or sulphuric acid.

In compounds having an esterified carboxy group as substituent, the latter can be converted into the corresponding carbamoyl group in customary manner, for example by ammonolysis or aminolysis with ammonia or a primary or secondary amine.

Compounds having a carbamoyl group and radicals $R_1$ and $R_2$ that are different from hydrogen can be dehydrated to form the corresponding cyano compounds in customary manner, for example by the action of dehydrating agents, such as phosphorus pentoxide, phosphorus oxychloride or trifluoroacetic acid anhydride, preferably at elevated temperatures.

In compounds having an esterified carboxy group as substituent and radicals $R_1$ and $R_2$ that are preferably different from hydrogen, the esterified carboxy group can be converted into a cyano group in customary manner, for example by the action of an organic aluminium amide compound, such as a di-lower alkylaluminium amide compound, for example diethylaluminium amide.

Compounds having radicals $R_1$ and $R_2$ that are different from hydrogen and containing a cyano substituent can be hydrolysed to the corresponding carbamoyl compounds or directly to the carboxy compounds in customary manner, for example in the presence of concentrated aqueous mineral acids or alkali metal hydroxides.

Compounds having a cyano group as substituent can be alcoholysed to form corresponding compounds having esterified carboxy groups in customary manner, for example by the addition of alcohols in the presence of an anhydrous acid, such as hydrogen chloride, and subsequent hydrolysis of the resulting imido ester.

Compounds of the formula I in which Ar contains as ring member the group —NH— can be converted into compounds of the formula I in which Ar contains as ring member a tertiary amino group by introducing a substituent, for example an optionally substituted lower alkyl group, such as methyl or benzyl, in customary manner, for example using a corresponding reactive esterified alcohol, such as a corresponding halide, for example chloride or bromide, or a diazoalkane, for example diazomethane.

Compounds in which Ar contains as ring member at least one tertiary nitrogen atom can be converted into N-oxides in customary manner by treating with a peroxy compound, such as hydrogen peroxide, or an acid derivative thereof, such as peracetic acid or m-chloroperbenzoic acid.

Compounds that are in the form of N-oxides can be converted in a manner known per se into the non-N-oxidised compounds, for example by means of sulphurous acid, or phosphorus oxychloride, or more especially by means of hydrogen in the presence of a hydrogenation catalyst, for example a noble metal catalyst, such as platinum or palladium, and also Raney nickel.

Compounds that carry in the aromatic ring Ar a lower alkylthio group, for example a methylthio group, can be converted into the sulphur-free compounds by treating with suitable desulphurating agents, for example Raney nickel, in a suitable solvent, for example dioxan.

As in the manufacturing processes, when carrying out the additional steps, care must be taken that undesired side reactions which may result in the conversion of additional groupings do not occur.

The reactions described above may be carried out simultaneously or in succession, as desired, and also in any sequence. If necessary, they are carried out in the presence of diluents, condensation agents and/or catalytically active agents, at reduced or elevated temperature, in a closed vessel under pressure and/or in an inert gas atmosphere.

Depending on the process conditions and the starting materials, the novel compounds are obtained in free form or in the form of their salts which is likewise included in the scope of the invention, it being possible for the novel compounds or salts thereof also to be in the form of hemi-, mono-, sesqui- or poly-hydrates thereof. Acid addition salts of the novel compounds can be converted into the free compounds in a manner known per se, for example by treating with basic agents, such as alkali metal hydroxides, carbonates or bicarbonates, or ion exchangers. On the other hand, resulting free bases with organic or inorganic acids, for example with the mentioned acids, may form acid addition salts, there being used for the manufacture thereof especially those acids which are suitable for the formation of pharmaceutically acceptable non-toxic salts.

These or other salts, especially acid addition salts, of the novel compounds, such as, for example, oxalates or perchlorates, may also be used to purify the resulting free bases, by converting the free bases into salts, separating and purifying these, and liberating the bases from the salts again.

Depending on the starting materials and procedures chosen, the novel compounds may also be in the form of optical antipodes or racemates or, if they contain at least two asymmetric carbon atoms, also in the form of racemic mixtures. The starting materials may also be used in the form of specific optical antipodes.

Resulting racemic mixtures may be separated on the basis of the physical-chemical differences between the diastereoisomers, in known manner, for example by chromatography and/or fractional crystallisation, into the two stereoisomeric (diastereoisomeric) racemates.

Resulting racemates can be resolved into the antipodes according to methods known per se, for example by recrystallisation from an optically active solvent, by treatment with suitable micro-organisms or by reaction with an optically active substance that forms salts with the racemic compound, especially acids, and separating the salt mixture obtained in this manner, for example on the basis of differing solubility, into the diastereoisomeric salts from which the free antipodes can be liberated by the action of suitable agents. Especially customary optically active acids are, for example, the D- and L-forms of tartaric acid, di-O,O'-(p-toluoyl)-tartaric acid, maleic acid, mandelic acid, camphorsulphonic acid, glutamic acid, aspartic acid or guinic acid. Advantageously, the more active of the two antipodes is isolated.

The invention relates also to those embodiments of the process according to which a compound obtainable as an intermediate at any stage of the process is used as starting material and the remaining process steps are carried out, or the process is discontinued at any stage, or in which a starting material is formed under the reaction conditions, or in which a reactant is optionally in the form of its salts.

The starting materials used for carrying out the reactions according to the invention are advantageously those which result in the classes of end products given special mention at the beginning and especially in those end products which are specifically described or emphasised.

The starting materials are known or, if new, can be manufactured according to methods known per se, as stated above, for example analogously to the methods described in the examples. The invention relates also to novel starting materials. The invention relates also to intermediates that can be obtained in accordance with the process.

The novel compounds may be used, for example, in the form of pharmaceutical preparations which contain a pharmacologically active amount of the active substance, optionally together with pharmaceutically acceptable carriers which are suitable for enteral, for example oral, or parenteral administration, and may be inorganic or organic and solid or liquid. Thus, tablets or gelatin capsules are used which contain the active substance together with diluents, for example lactose, dextrose, sucrose, mannitol, sorbitol, cellulose and/or glycerine and/or lubricants, for example siliceous earth, talc, stearic acid or salts thereof, such as magnesium or calcium stearate, and/or polyethylene glycol. Tablets may also contain binders, for example magnesium aluminium silicate, starches, such as corn, wheat, rice or arrowroot starch, gelatin, tragacanth, methylcellulose, sodium carboxymethylcellulose and/or polyvinylpyrrolidone, and, if desired, disintegrators, for example starches, agar, alginic acid or a salt thereof, such as sodium alginate, and/or effervescing mixtures, or adsorbents, colouring substances, flavourings and sweeteners. The novel pharmacologically active compounds can also be used in the form of parenterally administrable preparations or infusion solutions. Such solutions are preferably isotonic aqueous solutions or suspensions, it being possible to manufacture these before use, for example in the case of lyophilised preparations which contain the active substance on its own or together with a carrier, for example mannitol. The pharmaceutical preparations can be sterilised and/or contain adjuncts, for example preservatives, stabilisers, wetting agents and/or emulsifiers, solubilisers, salts for regulating the osmotic pressure and/or buffers. The present pharmaceutical preparations which may, if desired, contain further pharmacologically active substances, are manufactured in a manner known per se, for example by means of conventional mixing, granulating, coating, dissolving or lyophilising processes, and contain from approximately 0.1% to 100%, especially from approximately 1% to approximately 50%, and, in the case of lyophilisates, up to 100%, of the active substance.

The dosage may depend on various factors, such as the manner of administration, the species, age and/or individual condition. Thus, the daily doses of β-receptor blockers of the formula I to be administered in one or several but preferably not more than 4, single doses in the case of oral administration to warm-blooded animals is between 0.03 and 3 mg/kg and for warm-blooded animals weighing approximately 70 kg preferably between approximately 0.02 g and approximately 0.2 g.

The following examples serve to illustrate the invention; temperatures are given in degrees Centigrade.

EXAMPLE 1

After the addition of 1 g of palladium-on-carbon catalyst (5%), a solution of 9.7 g of crude 1-[N-benzyl-2-(3-carbamoyl-4-hydroxyphenoxy)-ethylamino]-3-[4-[1-methyl-4-(trifluoromethyl)-1H-imidazol-2-yl]-phenoxy]-2-propanol in 100 ml of methanol is hydrogenated under normal conditions until the absorption of hydrogen has ceased, the reaction product partly precipitating out of the solution. The suspension is diluted with 200 ml of dioxane/methanol 1:1, heated and filtered through a filter aid. The filtrate is freed of solvent in a rotary evaporator and the residue is recrystallised twice from methanol, yielding 1-[2-(3-carbamoyl-4-hydroxyphenoxy)-ethylamino]-3-[4-[1-methyl-4-(trifluoromethyl)-1H-imidazol-2-yl]-phenoxy]-2-propanol having a melting point of 195°–197°.

After recrystallisation from acetonitrile, the monomethanesulphonate, which is obtained in the customary manner, has a melting point of 139°–142°.

The 1-[N-benzyl-2-(3-carbamoyl-4-hydroxyphenoxy)-ethylamino]-3-[4-[1-methyl-4-(trifluoromethyl)-1H-imidazol-2-yl]-phenoxy]-2-propanol required as starting material may be prepared as follows:

(a) 2 g of sodium hydride dispersion (55% in oil) are added, while cooling in an ice bath, to a solution of 12 g of 2-[4-(2,3-epoxypropoxy)-phenyl]-4-(trifluoromethyl)-imidazole (J. med. Chem. 20, 1024 (1977)) in 90 ml of dimethylformamide and the yellow suspension is stirred for 1½ hours at room temperature. After the addition of 8 ml of methyl iodide, stirring is continued for a further 12 hours at room temperature, the reaction mixture is subsequently poured into water and extracted several times with ethyl acetate. After separating off the organic phase and removing the solvent, the residue is dissolved in chloroform and filtered over silica gel. The filtrate is again concentrated by evaporation and the residue is recrystallized from ether/hexane, yielding 2-[4-(2,3-epoxypropoxy)-phenyl]-1-methyl-4-(trifluoromethyl)-imidazole having a melting point of 65°–68°.

(b) A solution of 5 g of 2-[4-(2,3-epoxypropoxy)-phenyl]-1-methyl-4-(trifluoromethyl)-imidazole and 4.7 g of 5-[2-(benzylamino)-ethoxy]-salicylamide in 100 ml of isopropanol is heated under reflux for 15 hours and the solvent is subsequently removed in a rotary evaporator. The crude 1-[N-benzyl-2-(3-carbamoyl-4-hydroxyphenoxy)-ethylamino]-3-[4-[1-methyl-4-(trifluoromethyl)-imidazol-2-yl]-phenoxy]-2-propanol, obtained in the form of an oil, is further processed in that form.

EXAMPLE 2

A solution of 5.0 g of 1-[2-(3-carbamoyl-4-hydroxyphenoxy)-N-benzylethylamino]-3-[4-[5-[(4-trifluoromethyl)-1-benzyl-1H-imidazol-2-yl]-2-furyl]-phenoxy]-2-propanol in 50 ml of methanol is hydrogenated in the presence of 1 g of palladium-on-carbon catalyst (5%) under normal pressure and at 50° until the absorption of hydrogen has ceased. The resulting suspension is boiled up with 1 liter of methanol and filtered while hot. The filtrate is concentrated to a small volume in a rotary evaporator, 1.3 g of methanesulphonic acid are added thereto, the solution is heated briefly and caused to crystallise by cooling. After again recrystallising the crude product from methanol the 1-[2-(3-carbamoyl-4-hydroxyphenoxy)-ethylamino]-3-[4-[5-[4-(trifluoromethyl)-1H-imidazol-2-yl]-2-furyl]-phenoxy]-2-propanol dimethanesulphonate having a melting point of 232°–234° is obtained.

The 1-[2-(3-carbamoyl-4-hydroxyphenoxy)-N-benzylethylamino]-3-[4-[5-[4-trifluoromethyl)-1-benzyl-1H-imidazol-2-yl]-2-furyl]-phenoxy]-2-propanol used as starting material may be prepared as follows:

(a) 64.0 g of 1,4-anisidine are made into a slurry in 370 ml of water and 172 ml of concentrated hydrochloric acid are added thereto. After cooling in an ice bath, a solution of 36.4 g of sodium nitrite in 120 ml of water is added dropwise, while stirring, over the course of one hour. After 1½ hours there are added first of all 84 g of sodium acetate, then a solution of 28.8 g of copper(II) chloride dihydrate in 160 ml of water and finally an emulsion of 100.8 g of furan-2-carboxaldehyde in 200 ml of water. The dark reaction mixture is stirred overnight in an ice bath and then for 7 days at room temperature. For working up, the reaction mixture is extracted several times with toluene, the combined organic phases are washed with water and dried, and the oil that remains after the removal of the solvent is filtered through silica gel with ethyl acetate/hexane 1:4. 5-(4-Methoxyphenyl)-furan-2-carboxaldehyde is thus obtained in the form of a crystallising oil, which is used in that form in the next step.

(b) A solution of 39.9 g of sodium acetate and 40.2 g of 1,1-dibromo-3,3,3-trifluoroacetone in 90 ml of water is heated under reflux for 30 minutes, then cooled to 0° and added, the whole quantity at once, to a solution of 30 g of 5-(4-methoxyphenyl)-furan-2-carboxaldehyde in 1 liter of methanol at 0°. At 5°–10°, 165 ml of concentrated ammonia solution are added dropwise over the course of 30 minutes. After stirring for 50 hours at room temperature the mixture is filtered and the residue is washed with chloroform whereupon the 2-[(4-trifluoromethyl)-1H-imidazol-2-yl]-5-(4-methoxyphenyl)-furan precipitates out in the form of a yellow crystallisate.

(c) 2.75 g of sodium hydride dispersion (55%) are added to a solution of 18.7 g of 2-[4-(trifluoromethyl)-1H-imidazol-2-yl]-5-(4-methoxyphenyl)-furan in 200 ml of dimethylformamide and the mixture is stirred for one hour at room temperature. After the addition of 10.8 g of benzyl bromide stirring is continued for a further 20 hours at room temperature, the solvent is subsequently removed in a high vacuum, the residue is suspended in ethyl acetate/hexane 1:4 and filtered over silica gel. The eluate is concentrated to dryness by evaporation and the resulting crude 2-[1-benzyl-4-(trifluoromethyl)-1H-imidazol-2-yl]-5-(4-methoxyphenyl)-furan is further processed as such.

(d) A solution of 19.6 g of 2-[1-benzyl-4-(trifluoromethyl)-imidazol-2-yl]-5-(4-methoxyphenyl)-furan and 8.1 g of D,L-methionine in 110 ml of methanesulphonic acid is stirred under nitrogen for 20 hours at 100°. After cooling, the reaction mixture is poured onto ice, the pH is adjusted to 8 with concentrated ammonia and the mixture is extracted several times with methylene chloride. Washing with water, drying and concentration by evaporation of the organic phase yield the crystalline 2-[1-benzyl-4-(trifluoromethyl)-1H-imidazol-2-yl]-5-(4-hydroxyphenyl)-furan which is used as such in the next step.

(e) A solution of 48.1 ml of 1N sodium hydroxide solution and 18.5 ml of water is added to a solution of 18.5 g of 2-[1-benzyl-4-(trifluoromethyl)-1H-imidazol-2-yl]-5-(4-hydroxyphenyl)-furan in 160 ml of dioxan and the mixture is stirred for 10 minutes at room temperature. After the addition of 13.3 g of epichlorohydrin, the mixture is stirred for a further 48 hours at room temperature, then filtered and the filter residue is washed with dioxan/water 1:1 and then with ether. After drying, 2-[4-(2,3-epoxypropoxy)-phenyl]-5-[1-benzyl-4-(trifluoromethyl)-1H-imidazol-2-yl]-furan is obtained in the form of a white crystallisate.

(f) A solution of 7.0 g of 2-[4-(2,3-epoxypropoxy)-phenyl]-5-[1-benzyl-4-(trifluoromethyl)-1H-imidazol-2-yl]-furan and 4-[2-benzylamino)-ethoxy]-salicylamide in 120 ml of isopropanol is stirred under reflux for 12 hours. After the addition of active carbon, the mixture is filtered while hot and the solvent is removed in a rotary evaporator. The residue is then chromatographed over silica gel with a mixture of chloroform/methanol/ammonia (350:50:1). After working up, 1-[2-(3-carbamoyl-4-hydroxyphenoxy)-N-benylethylamino]-3-[4-[5-(4-trifluoromethyl)-1-benzyl-1H-imidazol-2-yl]-2-furyl]-phenoxy]-2-propanol is obtained in the form of a yellowish foam which is further processed in that form.

EXAMPLE 3

A solution of 3 g of crude 1-[N-benzyl-2-(3-carbamoyl-4-hydroxyphenoxy)-ethylamino]-3-[4-[(4-trifluoromethyl)-1H-imidazol-2-yl]-phenoxy]-2-propanol in 30 ml of absolute methanol is hydrogenated in the presence of 0.5 g of palladium-on-carbon catalyst (5%) under normal pressure and at room temperature until the absorption of hydrogen has ceased. The resulting suspension is diluted with 30 ml of methanol, heated under reflux and filtered while hot. The filtrate is freed of solvent in a rotary evaporator and the residue is recrystallised from isopropanol. 1-[2-(3-carbamoyl-4-hydroxyphenoxy)-ethylamino]-3-[4-[4-(trifluoromethyl)-1H-imidazol-2-yl]-phenoxy]-2-propanol having a melting point of 155°–158° is obtained.

The 1-[N-benzyl-2-(3-carbamoyl-4-hydroxyphenoxy)-ethylamino]-3-[4-[(4-trifluoromethyl)-1H-imidazol-2-yl]-phenoxy]-2-propanol used as starting material may be prepared as follows:

A solution of 1.8 g of 2-[4-(2,3-epoxypropoxy)-phenyl]-(4-trifluoromethyl)-imidazole (J. Med. Chem. 20, 1024 (1977)) and 1.8 g of 4-[2-(benzylamino)-ethoxy]-salicylamide in 100 ml of isopropanol is heated under reflux for 15 hours and the solvent is subsequently removed in a rotary evaporator. The oily residue is taken up in ethyl acetate and filtered over silica gel. The crude 1-[N-benzyl-2-(3-carbamoyl-4-hydroxyphenoxy)-ethylamino]-3-[4-(4-trifluoromethyl)-1H-imidazol-2-ylphenoxy]-2-propanol, obtained after removal of the solvent, is further processed in that form.

EXAMPLE 4

A solution of 13.2 g of crude 1-[N-benzyl-[2-(3-carbamoyl-4-hydroxyphenoxy)-ethylamino]]-3-[4-(4-acetyl-1,5-dimethyl-1H-imidazol-2-yl)-phenoxy]-2-propanol in 140 ml of methanol is hydrogenated with the addition of 1.3 g of palladium-on-carbon catalyst until 1 molar equivalent of hydrogen has been absorbed. After filtration and evaporation of the solvent, an oil is obtained which, after recrystallising twice from ethanol, yields 1-[2-(3-carbamoyl-4-hydroxyphenoxy)-ethylamino]-3-[4-(4-acetyl-1,5-dimethyl-1H-imidazol-2-yl)-phenoxy]-2-propanol having a melting point of 128°-130°.

The starting material is prepared in the following manner:

(a) Analogously to the process described by H. Lettau (Z. Chem. 10, 338, 1970 and ibid. 11, 10, 1971), 4-acetyl-1,5-dimethyl-2-(4-hydroxyphenyl)-1H-imidazole having a melting point of 198°-202° is obtained, in the form of a crude product, using 3-hydroximinopentane-2,4-dione, 4-hydroxybenzaldehyde and methylamine in acetic acid.

(b) A mixture of 11.5 g of 4-acetyl-1,5-dimethyl-2-(4-hydroxyphenyl)-1H-imidazole, 13.8 g of potassium carbonate, 7.0 g of epichlorohydrin and 120 ml of dimethylformamide is stirred for 20 hours in a bath at 60°-70°. The insoluble material is filtered off, the filtrate is concentrated by evaporation and the residue is divided between ethyl acetate and water. From the organic phase there is obtained, by concentration by evaporation, an oil which is chromatographed on silica gel with ethyl acetate. 4-acetyl-1,5-dimethyl-2-[4-(2,3-epoxypropoxy)-phenyl]-1H-imidazole is obtained from the first six fractions eluted in the form of a yellow oil.

(c) A solution of 8 g of crude 4-acetyl-1,5-dimethyl-2-[4-(2,3-epoxypropoxy)-phenyl]-1H-imidazole in 80 ml of isopropanol is boiled under reflux for 18 hours with 7.2 g of 5-(2-benzylaminoethoxy)-salicylamide. Concentration by evaporation yields 1-[N-benzyl-[2-(3-carbamoyl-4-hydroxyphenoxy)-ethylaminol]]-3-[4-(4-acetyl-1,5-dimethyl-1H-imidazol-2-yl)-phenoxy]-2-propanol in the form of a yellow foam which is further processed in the form of the crude product.

EXAMPLE 5

A solution of 13.1 g of crude 1-[N-benzyl-2-(3-carbamoyl-4-hydroxyphenoxy)-ethylamino]-3-[4-[4-methyl-6-(trifluoromethyl)-pyrimidin-2-yl]-phenoxy]-2-propanol hydrochloride is hydrogenated and worked up analogously to Example 1. The free base is precipitated out from the resulting solution of the hydrochloride by means of potassium bicarbonate in aqueous methanol. After recrystallisation from methylcellosolve, 1-[2-(3-carbamoyl-4-hydroxyphenoxy)-ethylamino]-3-[4-[4-methyl-6-(trifluoro-methyl)-pyrimidin-2-yl]-phenoxy]-2-propanol having a melting point of 227°-229° is obtained.

The starting material may be prepared in the following manner:

(a) In a pressure tube a mixture of 17.2 g of 4-hydroxybenzamidine dihydrate, 60 ml of ethanol and 14.6 ml of trifluoroacetylacetone is heated for 18 hours at a bath temperature of 110°. The mixture is then stirred with 200 ml of ether, a small amount of precipitate is filtered off with suction and the filtrate is extracted with two portions of 2N sodium hydroxide solution. The alkaline solution is treated with carbon, filtered and then 400 ml of ethyl acetate and 160 ml of 2N hydrochloric acid are added to pH 1. The organic phase is separated off, washed with water, dried over sodium sulphate and concentrated by evaporation. The residue is recrystallised from ether/hexane yielding 2-(4-hydroxyphenyl)-4-methyl-6-(trifluoromethyl)-pyrimidine having a melting point of 131°-132° C.

(b) The mixture of 17.0 g of 2-(4-hydroxyphenyl)-4-methyl-6-(trifluoromethyl)-pyrimidine, 23.1 g of potassium carbonate and 135 ml of epichlorohydrin is stirred at a temperature of 130° for 1.5 hours, then filtered with suction while hot; the filter residue is subsequently washed with methylene chloride and the filtrate is evaporated to dryness under reduced pressure. The residue is recrystallised from isopropanol and yields 2-[4-(2,3-epoxypropoxy)-phenyl]-4-methyl-6-(trifluoromethyl)-pyrimidine having a melting point of 97°-99°.

(c) 9.3 g of the resulting 2-[4-(2,3-epoxypropoxy)-phenyl]-4-methyl-6-(trifluoromethyl)-pyrimidine and 8.15 g of 5-[2-(benzylamino)-ethoxy]-salicylamide are stirred in 130 ml of isopropanol at a bath temperature of 70° for 15 hours. 10 ml of 3.5N ethereal hydrochloric acid and 600 ml of ether are added, whereupon the crude 1-[N-benzyl-2-(3-carbamoyl-4-hydroxyphenoxy)-ethylamino]-3-[4-[4-methyl-6-(trifluoromethyl)-pyrimidin-2-yl]-phenoxy]-2-propanol hydrochloride is obtained, first of all in oily form and then in the form of a yellow powder.

EXAMPLE 6

16 g of crude 1-[N-benzyl-2-(3-carbamoyl-4-hydroxyphenoxy)-ethylamino]-3-[4-(4,6-dimethylpyrimidin-2-yl)-phenoxy]-2-propanol hydrochloride are hydrogenated analogously to Example 1 and the free base is isolated according to Example 5. After recrystallisation from methylcellosolve, 1-[2-(3-carbamoyl-4-hydroxyphenoxy)-ethylamino]-3-[4-(4,6-dimethylpyrimidin-2-yl)-phenoxy]-2-propanol having a melting point of 209°-211° is obtained.

The starting material may be obtained in the following manner:

(a) 4,6-dimethyl-2-(4-hydroxyphenyl)-pyrimidine is reacted with epichlorohydrin in the presence of potassium carbonate analogously to Example 5b). After working up, 4,6-dimethyl-2-[4-(2,3-epoxypropoxy)-phenyl]-pyrimidine is obtained which, after recrystallisation from isopropanol, has a melting point of 88°-90°.

(b) The resulting 4,6-dimethyl-2-[4-(2,3-epoxypropoxy)phenyl]-pyrimidine is reacted with 5-[2-benzylaminoethoxy]-salicylamide in isopropanol analogously to Example 5c). After working up, the crude 1-[N-benzyl-2-(3-carbamoyl-4-hydroxyphenoxy)-ethylamino]-3-[4-(4,6-dimethylpyrimidin-2-yl)-phenoxy]-2-propanol hydrochloride is obtained in the form of a beige powder which is further used in that form.

EXAMPLE 7

11.6 g of 1-[N-benzyl-2-(3-carbamoyl-4-hydroxyphenoxy)-ethylamino]-3-[4-(3,5-dicarboethoxy-2,6-dimethylpyridin-4-yl)-phenoxy]-2-propanol are hydrogenated and worked up analogously to Example 1. The resulting base is reacted with fumaric acid in isopropanol and the resulting salt is recrystallised from ethanol. After drying for 15 hours at 0.05 mm Hg and 80°, 1-[2-(3-carbamoyl-4-hydroxyphenoxy)-ethylamino]-3-[4-(3,5-dicarboethoxy-2,6-dimethylpyridin-4-yl)-phenoxy]-2-propanol is obtained in the form of a neutral fumarate with ¼ mole of water of crystallisation and has a melting point of 133°-135°.

The starting material may be prepared in the following manner:

(a) 19.8 g of 2,6-dimethyl-4-(4-hydroxyphenyl)-1,4-dihydropyridine-3,5-dicarboxylic acid ethyl ester are melted with 3.7 g of sulphur for 30 minutes at a bath temperature of 220°. The reaction mass is dissolved in boiling acetonitrile and the solution is treated with carbon. On cooling, the 2,6-dimethyl-4-(4-hydroxyphenyl)-pyridine-3,5-dicarboxylic acid diethyl ester, which still contains excess sulphur, crystallises out. The majority of the sulphur is removed by heating at 90° and 0.05 mm Hg in a sublimation apparatus and the product subsequently melts at 172°–174°.

(b) 9.0 g of the resulting 2,6-dimethyl-4-(4-hydroxyphenyl)-pyridine-3,5-dicarboxylic acid diethyl ester are dissolved in a solution prepared from 0.723 g of sodium metal and 80 ml of ethanol. This solution is slowly added drop-wise to a boiling solution of 11.9 ml of epichlorohydrin in 80 ml of ethanol; after cooling, the sodium chloride that is deposited is filtered off with suction and the filtrate is concentrated to dryness by evaporation. The residue is dissolved in ether and washed in succession with aqueous 1N sodium hydroxide solution, 1N hydrochloric acid, saturated aqueous potassium bicarbonate solution and finally with water. After distilling off the ether, the crude 2,6-dimethyl-4-[4-(2,3-epoxypropoxy)-phenyl]-pyridine-3,5-dicarboxylic acid diethyl ester is obtained in the form of a yellow oil.

(c) The resulting 2,6-dimethyl-4-[4-(2,3-epoxypropoxy)-phenyl]-pyridine-3,5-dicarboxylic acid diethyl ester is reacted with 5-[2-benzylaminoethoxy]-salicylamide in isopropanol analogously to Example 5c).

The resulting hydrochloride is converted into the free base with aqueous saturated potassium bicarbonate solution, the free base being 1-[N-benzyl-2-(3-carbamoyl-4-hydroxyphenoxy)-ethylamino]-3-[4-(3,5-dicarboethoxy-2,6-dimethylpyridin-4-yl)-phenoxy]-2-propanol, and is further processed in that form.

EXAMPLE 8

After the addition of 0.3 g of palladium-on-carbon catalyst (5%), a solution of 0.95 g of crude 1-[N-benzyl-2-(3-carbamoyl-4-benzyloxyphenoxy)-ethylamino]-3-[4-[1-methyl-4-(trifluoromethyl)-1H-imidazol-2-yl]-phenoxy]-2-propanol in 10 ml of methanol is hydrogenated under normal conditions until the absorption of hydrogen has ceased, the reaction product partly precipitating out of the solution. The suspension is diluted with 20 ml of dioxan/methanol 1:1, heated and filtered through a filter aid. The filtrate is concentrated by evaporation and the residue is recrystallised twice from methanol, yielding the 1-[2-(3-carbamoyl-4-hydroxyphenoxy)-ethylamino]-3-[4-[1-methyl-4-(trifluoromethyl)-1H-imidazol-2-yl]-phenoxy]-2-propanol having a melting point of 195°–197°.

The starting material may be prepared, for example, as follows:

(a) 57.3 g of 5-[2-benzylaminoethoxy]-salicylamide are dissolved in 280 ml of dimethylformamide and 8.8 g of sodium hydride are added thereto in portions. After two hours a solution of 25.5 ml of benzyl chloride in 40 ml of dimethylformamide is added dropwise and stirring is continued again for two hours. The reaction mixture is then poured onto 2.8 liters of ice water and extracted in succession with ethyl acetate and ether. The organic phase is washed with 2N sodium hydroxide solution, then with water, and treated with carbon. 200 ml of 2N hydrochloric acid are added to the organic filtrate, the mixture is stirred for 15 minutes and the hydrochloride that precipitates out is filtered off with suction. The hydrochloride is washed with water, ethyl acetate and then with ether and then dissolved in 600 ml of hot methanol. After the addition of 650 ml of ether, 2-benzyloxy-5-[2-benzylaminoethoxy]-benzamide hydrochloride having a melting point of 200°–203° is obtained.

(b) Analogously to Example 5(c), 31.3 g of 2-benzyloxy-5-[2-(benzylamino)-ethoxy]-benzamide are reacted with 17.7 g of 4-(2,3-epoxypropoxy)-benzaldehyde in 500 ml of isopropanol to form 1-[N-benzyl-2-(3-carbamoyl-4-benzyloxyphenoxy)-ethylamino]-3-(4-formylphenoxy)-2-propanol hydrochloride.

(c) 5.25 g of 1,1,1-trifluoro-3,3-dibromoacetone are added to a solution of 5.25 g of crystallised sodium acetate in 20 ml of water and the mixture is stirred for 1 hour at 100°. The reaction mixture is then added, the whole quantity at once, to a solution of 8.9 g of 1-[N-benzyl-2-(3-carbamoyl-4-benzyloxyphenoxy)-ethylamino]-3-(4-formylphenoxy)-2-propanol in 180 ml of methanol at room temperature. 24 ml of concentrated ammonia (approximately 25%) are then added dropwise at 15°–20° (cooling with an ice bath) over a period of 10 minutes. After stirring for 48 hours at room temperature, the reaction mixture is concentrated by evaporation. The residue is dissolved in water and the solution is extracted with ethyl acetate; the organic phase is washed with saturated aqueous sodium chloride solution and dried over sodium sulphate. The oil that remains behind after removal of the solvent is filtered with chloroform/methanol 95:5 over silica gel. The 1-[N-benzyl-2-(3-carbamoyl-4-benzyloxyphenoxy)-ethylamino]-3-[4-[4-(trifluoromethyl)-1H-imidazol-2-yl]-phenoxy]-2-propanol is thus obtained in the form of an oil which is used in that form in the next step.

(d) At 0°, 0.18 g of potassium tert.-butoxide is added to a solution of 1.0 g of 1-[N-benzyl-2-(3-carbamoyl-4-benzyloxyphenoxy)-ethylamino]-3-[4-[4-(trifluoromethyl)-1H-imidazol-2-yl]-phenoxy]-2-propanol in 5 ml of dimethylformamide and the mixture is stirred for 20 minutes in an ice bath. At 0°–5°, a solution of 0.12 ml of methyl iodide in 3 ml of dimethylformamide is added and the mixture is then stirred for 4 hours at room temperature. The reaction solution is concentrated by evaporation, the residue is dissolved in water and the solution is extracted with ethyl acetate. After drying the organic phase over sodium sulphate, this is concentrated to dryness by evaporation, yielding the crude 1-[N-benzyl-2-(3-carbamoyl-4-benzyloxyphenoxy)-ethylamino]-3-[4-[1-methyl-4-(trifluoromethyl)-1H-imidazol-2-yl]-phenoxy]-2-propanol which is further processed in that form.

EXAMPLE 9

After the addition of 1 g of palladium-on-carbon catalyst (5%), a solution of 10.2 g of 1-[N-benzyl-2-(3-carbamoyl-4-hydroxyphenoxy)-ethylamino]-3-(4-biphenyloxy)-2-propanol in 300 ml of methanol is hydrogenated under normal conditions until the absorption of hydrogen has ceased, the reaction product partly precipitating out of the solution. The suspension is diluted with 1.4 liter of dioxan/methanol 1:1, heated and filtered through a filter aid. The filtrate is concentrated by evaporation and the residue is recrystallised twice from methanol, yielding the 1-[2-(3-carbamoyl-4-hydroxyphenoxy)-ethylamino]-3-(4-biphenyloxy)-2-propanol having a melting point of 191°–192°.

After recrystallisation from acetonitrile, the monomethanesulphonate, which is obtained in the customary manner, has a melting point of 169°–170°.

The 1-[N-benzyl-2-(3-carbamoyl-4-hydroxyphenoxy)-ethylamino]-3-(4-biphenyloxy)-2-propanol required as starting material may be prepared as follows:

(a) A suspension of 10 g of 4-hydroxybiphenyl and 10 g of pulverised potassium carbonate in 75 ml of epichlorohydrin is stirred under reflux from 4 hours. The reaction mixture is concentrated by evaporation, water is added to the residue and the mixture is extracted with ethyl acetate. The organic phase is dried over sodium sulphate and concentrated by evaporation. The residue is recrystallised from isopropanol, yielding 4-(2,3-epoxypropoxy)-biphenyl having a melting point of 86°–88°.

(b) A solution of 5.97 g of 4-(2,3-epoxypropoxy)-biphenyl and 6.87 g of 5-[2-(benzylamino)-ethoxy]-salicylamide in 140 ml of isopropanol is heated under reflux for 15 hours and the solvent is then removed in a rotary evaporator. The residue is recrystallised from diethyl ether, yielding 1-[N-benzyl-2-(3-carbamoyl-4-hydroxyphenoxy)-ethylamino]-3-(4-biphenyloxy)-2-propanol having a melting point of 135°–138°.

EXAMPLE 10

A solution of 0.85 g of crude 1-[N-benzyl-2-(3-carbamoyl-4-benzyloxyphenoxy)-ethylamino]-3-[4-[1-methyl-1H-imidazol-2-yl]-phenoxy]-2-propanol in 10 ml of methanol is hydrogenated analogously to Example 8. After working up, the 1-[2-(3-carbamoyl-4-hydroxyphenoxy)-ethylamino]-3-[4-(1-methyl-1H-imidazol-2-yl)-phenoxy]-2-propanol having a melting point of 108°–112° is obtained.

The 1-[N-benzyl-2-(3-carbamoyl-4-benzyloxyphenoxy)-ethylamino]-3-[4-[1-methyl-1H-imidazol-2-yl]-phenoxy]-2-propanol required as starting material may be obtained, for example, as follows:

Analogously to the procedure described in Example 8c), 8.9 g of 1-[N-benzyl-2-(3-carbamoyl-4-benzyloxyphenoxy)-ethylamino]-3-(4-formylphenoxy)-2-propanol are reacted, using 4.2 g of 3,3-dibromoacetone, to form 1-[N-benzyl-2-(3-carbamoyl-4-benzyloxyphenoxy)-ethylamino]-3-[4-[1H-imidazol-2-yl]-phenoxy]-2-propanol, from which there is obtained, analogously to Example 8d), 1-[N-benzyl-2-(3-carbamoyl-4-benzyloxyphenoxy)-ethylamino]-3-[4-[1-methyl-1H-imidazol-2-yl)-phenoxy]-2-propanol in the form of a crude product which is further processed in that form.

EXAMPLE 11

Analogously to the procedure described in Example 1, 9.7 g of crude 1-[N-benzyl-2-(4-carbamoyl-3-hydroxyphenoxy)-ethylamino]-3-[4-[1-methyl-4-(trifluoromethyl)-1H-imidazol-2-yl]-phenoxy]-2-propanol are converted, by means of hydrogenation, into the 1-[2-(4-carbamoyl-3-hydroxyphenoxy)-ethylamino]-3-[4-[1-methyl-4-(trifluoromethyl)-1H-imidazol-2-yl]-phenoxy]-2-propanol of which the monoethanesulphonate, obtained in the customary manner, has a melting point of 131°–136°.

The 1-[N-benzyl-2-(4-carbamoyl-3-hydroxyphenoxy)-ethylamino]-3-[4-[1-methyl-4-(trifluoromethyl)-1H-imidazol-2-yl]-phenoxy]-2-propanol required as starting material may be obtained according to Example 1b) from 5 g of 2-[4-(2,3-epoxypropoxy)-phenyl]-1-methyl-4-(trifluoromethyl)-imidazole and 4.7 g of 4-[2-(benzylamino)-ethoxy]-salicylamide; it is obtained in the form of a crude product that is further processed in that form.

EXAMPLE 12

A solution of 11.0 g of 5-(2-aminoethoxy)-salicylamide in 70 ml of dimethyl sulphoxide is heated to 70°, 19.5 g of 5-[4-(2,3-epoxypropoxy)-phenyl]-1-methyl-3-methylthio-1H-1,2,4-triazole are added thereto and the mixture is stirred for one hour at this temperature. The reaction mixture is poured onto 1000 ml of ice water. The crystals that are deposited after a few minutes are filtered off with suction and recrystallised from a large quantity of methanol. There is thus obtained 1-[2-(3-carbamoyl-4-hydroxyphenoxy)-ethylamino]-3-[4-(1-methyl-3-methylthio-1H-1,2,4-triazol-5-yl)-phenoxy]-2-propanol having a melting point of 180°–181°. A further quantity of this compound is obtained from the mother liquor by concentration.

The 5-[4-(2,3-epoxypropoxy)-phenyl]-1-methyl-3-methylthio-1H-1,2,4-triazole required as starting material may be prepared in the following manner:

(12a) Analogously to Example (15b), a mixture of 49.6 g of 1-methyl-3-methylthio-5-(4-methoxyphenyl)-1H-1,2,4-triazole, 40 g of L-methionine and 380 ml of methanesulphonic acid is heated for 24 hours in a bath at 110°–120° and analogously worked up, yielding 5-(4-hydroxyphenyl)-1-methyl-3-methylthio-1H-1,2,4-triazole having a melting point of 216°–220° (from isopropanol).

(12b) 27.2 g of the resulting compound and 30.5 g of potassium carbonate are stirred in 220 ml of epichlorohydrin under reflux for 10 minutes. The crude product obtained after working up analogously to Example (16d) is chromatographed on 500 g of silica gel and eluted with ether (200 ml fractions). The combined fractions 18–34 are concentrated by evaporation and recrystallised from ethyl acetate/petroleum ether, yielding 5-[4-(2,3-epoxypropoxy)-phenyl]-1-methyl-3-methylthio-1H-1,2,4-triazole having a melting point of 75°–76°.

EXAMPLE 13

With the addition of 5 g of palladium-on-carbon catalyst (5%), a solution of 21 g of crude 1-[N-benzyl[2-(3-carbamoyl-4-hydroxyphenoxy)-ethylamino]]-3-[2-indol-2-yl)-phenoxy]-2-propanol in 210 ml of methanol is hydrogenated and worked up analogously to Example 4. After recrystallisation from ethanol, 1-[2-(3-carbamoyl-4-hydroxyphenoxy)-ethylamino]-3-[2-(indol-2-yl)-phenoxy]-2-propanol is obtained having a melting point of 93°–95° and containing ½ mole of ethanol.

The starting compound is obtained in the following manner: (13a) A solution of 10.5 g of 2-[2-(2,3-epoxypropoxy)-phenyl]-indole and 10.2 g of 5-(2-benzylaminoethoxy)-salicylamide in 300 ml of isopropanol is reacted analogously to Example 4(c) and yields crude 1-[N-benzyl-[2-(3-carbamoyl-4-hydroxyphenoxy)-ethylamino]]-3-[2-(indol-2-yl)-phenoxy]-2-propanol in the form of an orange resin that is further processed in that form.

EXAMPLE 14

With the addition, in two portions, of a total of 10 g of palladium-on-carbon catalyst (5%), a solution of 25 g of crude 1-[N-benzyl-[2-(3-carbamoyl-4-hydroxyphenoxy)-ethylamino]]-3-[4-(1,4,5-trimethyl-1H-imidazol-2-yl)-phenoxy]-2-propanol in 250 ml of methanol is hydrogenated under normal pressure until the absorption of hydrogen has ceased. The hydrogenated solution, filtered and concentrated by evaporation, is chromatographed on 500 g of silica gel and eluted with chloroform/methanol (9:1) (each fraction=50 ml). Fractions 150–200 are combined and concentrated by evaporation and yield 1-[2-(3-carbamoyl-4-hydroxyphenoxy)-ethylamino]-3-[4-(1,4,5-trimethyl-1H-imidazol-2-yl)-phenoxy]-2-propanol in the form of a beige foam, of which the H-NMR spectrum (DMSO-d6) is consistent with the given structure.

The starting compound is prepared in the following manner:

(14a) Analogously to Example (4a), 2-(4-hydroxyphenyl)-1,4,5-trimethyl-1H-imidazole having a melting point of 270°–277° is obtained from 3-oximino-2-butanone, 4-hydroxybenzylaldehyde and methylamine in glacial acetic acid and by subsequent reduction with zinc dust.

(14b) Analogously to Example (4b), from the compound obtained according to Example (14a), 2-[4-(2,3-epoxypropoxy)-phenyl]-1,4,5-trimethyl-1H-imidazole is obtained in the form of an orange-brown oil which solidifies partly in crystalline form and produces a H-NMR spectrum (CDCl3) that is consistent with the supposed structure.

(14c) The reaction of 1.2 molar equivalents of the resulting crude compound with 1.0 molar equivalent of 5-(2-benzylaminoethoxy)-salicylamide according to Example (4c) yields 1-[N-benzyl-[2-(3-carbamoyl-4-hydroxyphenoxy)-ethylamino]]-3-[4-(1,4,5-trimethyl-1H-imidazol-2-yl)-phenoxy]-2-propanol in the form of an oil which is further processed in that form.

EXAMPLE 15

With the addition of 3.0 g of palladium-on-carbon catalyst (10%), a solution of 16 g of crude 1-[N-benzyl-[2-(3-carbamoyl-4-hydroxyphenoxy)-ethylamino]]-3-[4-(4-methyl-5-trifluoromethyl-4H-1,2,4-triazol-3-yl)-phenoxy]-2-propanol in 160 ml of methanol is catalytically hydrogenated under normal conditions until, after 35 hours, the calculated quantity of hydrogen has been absorbed (an additional quantity of 2 g of catalyst is required for this purpose). Filtration and concentration by evaporation of the filtrate produce a semi-solid mass which, by recrystallisation from isopropanol using active carbon, yields 1-[2-(3-carbamoyl-4-hydroxyphenoxy)-ethylamino]-3-[4-(4-methyl-5-trifluoromethyl-4H-1,2,4-triazol-3-yl)-phenoxy]-2-propanol having a melting point of 151°–153°.

The starting compound is obtained in the following manner:

(15a) 20 ml of triethylamine are added to a suspension of 12.8 g of trifluoroacetylhydrazine in 100 ml of chloroform. While stirring, a solution of 20 g of crude 4-methoxy-N-methylbenzimide chloride in 50 ml of chloroform is added dropwise in such a manner that the internal temperature does not exceed 40°–45°. The reaction mixture is stirred overnight at room temperature and then concentrated by evaporation. The residue is divided between ethyl acetate and 2N sodium carbonate solution, the organic phase is separated off, washed with water, dried over magnesium sulphate and concentrated by evaporation. The partly crystalline residue is stirred with ether, the crystals are filtered off and recrystallised twice from ethanol, yielding 3-(4-methoxyphenyl)-4-methyl-5-trifluoromethyl-4H-1,2,4-triazole having a melting point of 155°–160°.

(15b) 8.05 g of the resulting compound and 5.1 g of L-methionine are dissolved under nitrogen in 56 ml of methanesulphonic acid and heated in a bath at 120° for 48 hours. After cooling, the reaction mixture is poured onto approximately 200 ml of ice water and the pH is adjusted to 9–10 with concentrated ammonia solution, whereupon crude 3-(4-hydroxyphenyl)-4-methyl-5-trifluoromethyl-4H-1,2,4-triazole crystallises out: melting point 210°–212° (sinters above 204°).

(15c) While stirring, 6.9 g of the resulting compound, 11.8 g of potassium carbonate and 4.5 ml of epichlorohydrin are boiled under reflux in 100 ml of acetone for 20 hours. After the addition of a further 4.5 ml of epichlorohydrin and 11.8 g of potassium carbonate the reaction mixture is boiled for a further 24 hours. By filtration and concentration by evaporation, a brown, contaminated oil is obtained which, by treating with 100 ml of 2N sodium hydroxide solution and 1.0 g of tetrabutylammonium hydrogen sulphate in 200 ml of dichloromethane (15 hours at 20°), yields pure 3-[4-(2,3-epoxypropoxy)-phenyl]-4-methyl-5-trifluoromethyl-4H-1,2,4-triazole which, after recrystallisation from isopropanol, melts at 104°–106°.

(15d) 7.0 g of 5-(2-benzylaminoethoxy)-salicylamide and 8.5 g of the compound obtained according to Example (15c) are reacted and worked up analogously to Example (4c) and yield crude 1-[N-benzyl-[2-(3-carbamoyl-4-hydroxyphenoxy)-ethylamino]]-3-[4-(4-methyl-5-trifluoromethyl-4H-1,2,4-triazol-3-yl)-phenoxy]-2-propanol in the form of a foam that is further processed in crude form.

EXAMPLE 16

After the addition of 2 g of palladium-on-carbon catalyst (5%), a solution of 22 g of crude 1-[N-benzyl-[2-(3-carbamoyl-4-hydroxyphenoxy)-ethylamino]]-3-[4-(1-methyl-5-trifluoromethyl-1H-1,2,4-triazol-3-yl)-phenoxy]-2-propanol in 320 ml of methanol is hydrogenated under normal conditions until the calculated quantity of hydrogen has been absorbed (3 hours). The product, which has partly crystallised out, is made into a solution by the addition of 1000 ml of dioxan and heating, the catalyst is filtered off and the filtrate is concentrated by evaporation. The crystalline residue that remains is recrystallised from approximately 400 ml of dioxan and yields 1-[2-(3-carbamoyl-4-hydroxyphenoxy)-ethylamino]-3-[4-(1-methyl-5-(trifluoromethyl)-1H-1,2,4-triazol-3-yl)-phenoxy]-2-propanol having a melting point of 206°–208°.

The starting compound may be prepared in the following manner:

(16a) A solution of 80 g of ethyl-(4-methoxybenzimidate) and 23 g of methylhydrazine in 1000 ml of ethanol is boiled under reflux for 16–18 hours and subsequently concentrated by evaporation. The crystalline residue is recrystallised from a small quantity of isopropanol and yields 1-methyl-4'-methoxybenzamidrazone having a melting point of 111°–113°.

(16b) 33.6 g of trifluoroacetic acid anhydride are added dropwise, while stirring, to a solution of 25.5 g of the resulting compound in 250 ml of anhydrous dioxan. When the exothermic reaction has died away the reaction mixture is subsequently stirred for 2 hours and concentrated by evaporation; the residue is dissolved in 500 ml of toluene and the solution is heated overnight in a water separator with the addition of 1 ml of methanesulphonic acid. The toluene solution is then washed with 50 ml of 2N potassium bicarbonate solution, dried over magnesium sulphate and concentrated by evaporation. The crystalline residue that remains is recrystallised from ether/petroleum ether and yields 3-(4-methoxyphenyl)-1-methyl-5-trifluoromethyl-1H-1,2,4-triazole having a melting point of 82°–83°.

(16c) Analogously to the procedure described in Example (15b), from the resulting compound there is obtained 3-(4-hydroxyphenyl)-1-methyl-5-trifluoromethyl-1H-1,2,4-triazole having a melting point of 189°–190° (from ether).

(16d) 20.2 g of the compound obtained according to Example (16c) are added, while stirring, to a boiling suspension of 20.6 g of potassium carbonate in 150 ml of epichlorohydrin. The reaction mixture is boiled under reflux for 30–40 minutes, filtered while still warm and concentrated by evaporation. The resulting crude product is converted into pure 3-[4-(2,3-epoxypropoxy)-phenyl]-1-methyl-5-trifluoromethyl-1H-1,2,4-triazole analogously to Example (15c). After recrystallisation from isopropanol, this melts at 110°–111°.

(16e) Analogously to Example (4c), from 11.0 g of the compound obtained according to Example (16d) and 10.0 g of 5-(2-benzylaminoethoxy)-salicylamide, crude 1-[N-benzyl-[2-(3-carbamoyl-4-hydroxyphenoxy)-ethylamino]]-3-[4-(1-methyl-5-trifluoromethyl-1H-1,2,4-triazol-3-yl)-phenoxy]-2-propanol is obtained in the form of a viscous oil which is further used in that form.

EXAMPLE 17

24.3 g of crude 1-[N-benzyl-[2-(3-carbamoyl-4-hydroxyphenoxy)-ethylamino]]-3-[4-(1-methyl-3-methylsulphonyl-1H-1,2,4-triazol-5-yl)-phenoxy]-2-propanol are catalytically debenzylated analogously to Example (4) and for working up, the crystalline precipitate is dissolved in dioxan by heating. Recrystallisation from methanol/dioxan yields 1-[2-(3-carbamoyl-4-hydroxyphenoxy)-ethylamino]-3-[4-(1-methyl-3-methylsulphonyl-1H-1,2,4-triazol-5-yl)-phenoxy]-2-propanol having a melting point of 190°–191°.

The starting material may be obtained in the following manner:

(17a) While stirring and cooling with ice, 15.1 g of 3-chloroperbenzoic acid are added, in portions, to a solution of 11.5 g of the compound obtained according to Example (12b) in 200 ml of chloroform. After the slightly exothermic reaction has died away the reaction mixture is stirred at room temperature for 10–15 hours. The 3-chlorobenzoic acid that crystallises out is filtered off and the filtrate is washed with 50 ml of an aqueous sodium sulphite solution (5%) then twice with 50 ml of potassium carbonate solution each time, dried over magnesium sulphate and concentrated by evaporation. Crude 5-[4-(2,3-epoxypropoxy)-phenyl]-1-methyl-3-methylsulphonyl-1H-1,2,4-triazole is obtained in the form of a yellow oil which is further used in that form.

(17b) 13 g of the resulting crude compound and 10.6 g of 5-(2-benzylaminoethoxy)-salicylamide in 150 ml of isopropanol are reacted analogously to the procedure described in Example (4c) and yield crude 1-[N-benzyl-[2-(3-carbamoyl-4-hydroxyphenoxy)-ethylamino]]-3-[4-(1-methyl-3-methylsulphonyl-1H-1,2,4-triazol-5-yl)-phenoxy]-2-propanol in the form of an orange oil which is catalytically debenzylated without further purification.

EXAMPLE 18

Analogously to the procedure described in Example 12, by reacting 2.3 g of 5-[4-(2,3-epoxypropoxy)-phenyl]-2-methyl-2H-tetrazole with 1.5 g of 5-(2-aminoethoxy)-salicylamide there is obtained 1-[2-(3-carbamoyl-4-hydroxyphenoxy)-ethylamino]-3-[4-(2-methyl-2H-tetrazol-5-yl)-phenoxy]-2-propanol having a melting point of 174°–175° (from dioxan).

(18a) The 5-[4-(2,3-epoxypropoxy)-phenyl]-2-methyl-2H-tetrazole required as starting material may be prepared in the following manner:

While stirring and cooling with ice, 2.86 g of sodium hydride suspension (55%) are added, in portions, to a solution of 11 g of 5-(4-methoxyphenyl)-tetrazole in 100 ml of dimethylformamide and the mixture is then stirred for 30 minutes at an internal temperature of 40°–50°. The mixture is then cooled to approximately 25° and 4.3 ml of methyl iodide are added dropwise within a period of approximately 10 minutes. After the exothermic reaction has died away the reaction mixture is stirred for 30 minutes, filtered and concentrated by evaporation. The residue is stirred with 100 ml of water. The crystalline precipitate is filtered off and recrystallised from a small quantity of isopropanol. The crystals thus obtained form a mixture that consists predominantly of 5-(4-methoxyphenyl)-2-methyl-2H-tetrazole and melts at 72°–80°.

(18b) 63.6 g of the resulting compound and 97.5 g of DL-methionine are dissolved in 570 ml of methanesulphonic acid and stirred under nitrogen for 18 hours in a bath at 110°–120°. The reaction mixture is poured onto ice water and rendered alkaline with concentrated ammonia. The crystals that are precipitated are filtered off with suction and recrystallised from a small quantity of isopropanol, yielding pure 5-(4-hydroxyphenyl)-2-methyl-2H-tetrazole.

(18c) A suspension of 17.6 g of the compound obtained according to (18b) and 30 g of potassium carbonate in 180 ml of epichlorohydrin is heated under reflux for 30 minutes. Working up analogously to Example (15c) produces 23 g of an oil which is filtered over 250 g of silica gel by means of dichloromethane and yields 5-[4-(2,3-epoxypropoxy)-phenyl]-2-methyl-2H-tetrazole having a melting point of 93°–94°.

EXAMPLE 19

A mixture of 1.5 g of 1-amino-3-[4-(1-methyl-4-(trifluoromethyl)-1H-imidazol-2-yl)-phenoxy]-2-propanol and 0.82 g of 5-(2-bromoethoxy)-salicylamide is stirred for 1 hour in an oil bath at a temperature of 100°. The melt is then extracted by boiling with 30 ml of isopropanol. The filtered solution is concentrated to 15 ml, cooled and the crystals that are precipitated are filtered off. Recrystallisation from methanol yields 1-[2-(3-carbamoyl-4-hydroxyphenoxy)-ethylamino]-3-[4-(1-methyl-4-(trifluoromethyl)-1H-imidazol-2-yl)-phenoxy]-2-propanol having a melting point of 195°–197°.

The 1-amino-3-[4-(1-methyl-4-(trifluoromethyl)-1H-imidazol-2-yl)-phenoxy]-2-propanol used as starting material may be prepared in the following manner:

(19a) 3.0 g of the compound obtained according to Example (1a) and 2.4 g of dibenzylamine are heated under reflux in 30 ml of isopropanol for 10 hours. The residue from concentration by evaporation consists of oily 1-(dibenzylamino)-3-[4-(1-methyl-4-(trifluoromethyl)-1H-imidazol-2-yl)phenoxy]-2-propanol which is processed without further purification.

(19b) With the addition of 1.0 g of palladium-on-carbon catalyst (5%), a solution of 5.5 g of the resulting crude compound in 120 ml of methanol is hydrogenated until 1 molar equivalent of hydrogen has been absorbed. Filtration and concentration by evaporation of the solution yields crude 1-amino-3-[4-(1-methyl-4-(trifluoromethyl)-1H-imidazol-2-yl)-phenoxy]-2-propanol in the form of an oil of which the proton resonance spectrum is consistent with its supposed structure.

EXAMPLE 20

A solution of 3.9 g of 5-(2-aminoethoxy)-salicylamide in 30 ml of dimethyl sulphoxide is heated to 70° and 7.2 g of 2-[4-(2,3-epoxypropoxy)-phenyl]-1-methyl-4-(trifluoromethyl)-1H-imidazole are added. The reaction mixture is stirred for 1 hour at 70° and worked up analogously to Example 12. 1-[2-(3-carbamoyl-4-hydroxyphenoxy)-ethylamino]-3-[4-(1-methyl-4-(trifluoromethyl)-1H-imidazol-2-yl)-phenoxy]-2-propanol having a melting point of 195°–197° is obtained (from methanol).

The 2-[4-(2,3-epoxypropoxy)-phenyl]-1-methyl-4-(trifluoromethyl)-1H-imidazole used as starting material may be prepared in the following manner:

(20a) 48.1 g of ammonium acetate and 300 ml of concentrated ammonia are added to a solution of 81.6 g of 4-methoxybenzaldehyde in 1.5 liters of methanol and 300 ml of water. 81.0 g of 3,3-dibromotrifluoroacetone are then added dropwise at room temperature and the reaction mixture is subsequently stirred for 18 hours. The methanol is removed in a rotary evaporator, the aqueous emulsion that remains behind is extracted several times with ethyl acetate, the organic phase is dried and concentrated to a small volume. The addition of hexane and cooling in an ice bath causes the product to crystallise. After filtering off and drying in vacuo at 60°, 2-(4-methoxyphenyl)-4-(trifluoromethyl)-imidazole having a melting point of 197°–202° is obtained. (20b) At an internal temperature of 0°–5°, first of all 5.62 g of potassium tert.-butoxide are added to a solution of 11.14 g of 2-(4-methoxyphenyl)-4-(trifluoromethyl)-imidazole in 107 ml of dimethylformamide. After 20 minutes, a solution of 3.8 ml of methyl iodide in 15 ml of dimethylformamide is slowly added, dropwise, while stirring and the reaction mixture is then stirred at room temperature for a further 4 hours. After removing the dimethylformamide in a rotary evaporator, the residue is made into a slurry with water and the aqueous phase is extracted several times with ethyl acetate. The combined organic phases are dried over sodium sulphate, concentrated to a small volume and hexane is added until crystallisation begins. After filtering and drying in vacuo, 2-(4-methoxyphenyl)-1-methyl-4-(trifluoromethyl)-imidazole having a melting point of 87°–88° is obtained.

(A mixture of 2-(4-methoxyphenyl)-1-methyl-4-(trifluoromethyl)-imidazole and 2-(4-methoxyphenyl)-1-methyl-(5-trifluoromethyl)-imidazole is detected in the mother liquors. This mixture is used in the following step 20c) and afterwards is separated into the resulting isomeric phenols.)

(20c) 9.3 g of 2-(4-methoxyphenyl)-1-methyl-4-(trifluoromethyl)-imidazole are dissolved in a mixture of 46.1 ml of acetic acid and 46.5 ml of 48% strength hydrobromic acid and the solution is heated under reflux for 48 hours. The solution is concentrated in a rotary evaporator to form a thick paste which is diluted with water; the pH is adjusted to 11 with concentrated ammonia and finally extraction is carried out several times with ethyl acetate. After drying the organic phase and filtration, concentration is carried out in a rotary evaporator until a thick suspension is produced. After cooling, the suspension is filtered and the crystallisate is dried in vacuo, yielding the 2-(4-hydroxyphenyl)-1-methyl-4-(trifluoromethyl)-1H-imidazole having a melting point of 220°–221°.

In analogous manner, from the mother liquors described at the end of Example (20b) there is obtained a mixture of 2-4-hydroxyphenyl)-1-methyl-4-(trifluoromethyl)-1H-imidazole and 2-(4-hydroxyphenyl)-1-methyl-5-(trifluoromethyl)-1H-imidazole, which can be separated by recrystallising several times from ethyl acetate, the resulting 2-(4-hydroxyphenyl)-1-methyl-5-(trifluoromethyl)-1H-imidazole having a melting point of 173°–174°.

(20d) 40 g of 2-(4-hydroxyphenyl)-1-methyl-4-(trifluoromethyl)-1H-imidazole and 40 g of anhydrous potassium carbonate are suspended in 400 ml of epichlorohydrin and the suspension is heated under reflux for 35 minutes. After cooling the reaction mixture in an ice bath, it is filtered and the filtrate is concentrated in a rotary evaporator. The oil that remains behind is dissolved in ether, the solution is treated with active carbon, filtered and cooled in an ice/sodium chloride bath. 2-[4-(2,3-epoxypropoxy)-phenyl]-1-methyl-4-(trifluoromethyl)-1H-imidazole crystallises out and is filtered and dried. Melting point 69°–70°.

EXAMPLE 21

After the addition of 1 g of palladium-on-carbon catalyst (5%), a solution of 19.4 g of crude 1-[N-benzyl-2-(3-carbamoyl-4-hydroxyphenoxy)-ethylamino]-3-[4-[1-methyl-5-(trifluoromethyl)-1H-imidazol-2-yl]-phenoxy]-2-propanol in 100 ml of methanol is hydrogenated under normal conditions until the absorption of hydrogen has ceased. The catalyst is filtered off, the filtrate is concentrated in a rotary evaporator and the oil that remains behind is chromatographed on a silica gel column with a mixture of chloroform/methanol/ammonia in the volume ratio 40:10:1. The product isolated from the main fractions is recrystallised once from isopropanol, then dissolved in methanol; an equivalent quantity of methanesulphonic acid is added to the solution and, after treatment with animal charcoal and filtration, ethyl acetate is added until crystallisation begins. After cooling in an ice bath, the mixture is filtered and yields 1-[2-(3-carbamoyl-4-hydroxyphenoxy)-ethylamino]-3-[4-[1-methyl-5-(trifluoromethyl)-1H-imidazol-2-yl]-phenoxy]-2-propanol methanesulphonate having a melting point of 126°–130°.

The 1-[N-benzyl-2-(3-carbamoyl-4-hydroxyphenoxy)-ethylamino]-3-[4-[1-methyl-5-(trifluoromethyl)-imidazol-2-yl]-phenoxy]-2-propanol required as starting material may be prepared as follows:

(21a) 25 g of the 2-(4-hydroxyphenyl)-1-methyl-5-(trifluoromethyl)-1H-imidazole obtained according to Example (20c) and 25 g of anhydrous potassium carbonate are suspended in 250 ml of epichlorohydrin and the mixture is heated under reflux for 10 minutes. The mixture is subsequently filtered and excess epichlorohydrin is removed in a rotary evaporator. The residue is dissolved in ether, the solution is stirred with silica gel and active carbon, the solution is filtered and hexane is added until crystallisation begins. After filtration, 2-[4-(2,3-epoxypropoxy)-phenyl]-1-methyl-5-(trifluoromethyl)-1H-imidazole is obtained in the form of a colourless crystallisate having a melting point of 99°–101°.

(21b) A solution of 5 g of the resulting 2-[4-(2,3-epoxypropoxy)-phenyl]-1-methyl-5-(trifluoromethyl)-1H-imidazole and 4.7 g of 5-[2-(benzylamino)-ethoxy]-salicylamide in 100 ml of isopropanol is heated under reflux for 15 hours and the solvent is subsequently removed in a rotary evaporator. The crude 1-[N-benzyl-2-(3-carbamoyl-4-hydroxyphenoxy)-ethylamino]-3-[4-[1-methyl-5-(trifluoromethyl)-1H-imidazol-2-yl]-phenoxy]-2-propanol obtained in the form of an oil is further processed in that form.

EXAMPLE 22

After the addition of 1 g of palladium-on-carbon catalyst (5%), a solution of 11 g of crude 1-[N-benzyl-2-(3-carbamoyl-4-hydroxyphenoxy)-ethylamino]-3-[4-[1-isopropyl-4-(trifluoromethyl)-1H-imidazol-2-yl]-phenoxy]-2-propanol in 100 ml of methanol is hydrogenated under normal conditions until the absorption of hydrogen has ceased. The catalyst is filtered off, the solvent is removed in a rotary evaporator and the residue is recrystallised twice from isopropanol. After filtering off and drying the crystals, 1-[2-(3-carbamoyl-4-hydroxyphenoxy)-ethylamino]-3-[4-[1-isopropyl-4-(trifluoromethyl)-1H-imidazol-2-yl]-phenoxy]-2-propanol having a melting point of 143°–145° is obtained.

The 1-[N-benzyl-2-(3-carbamoyl-4-hydroxyphenoxy)-ethylamino]-3-[4-[1-isopropyl-4-(trifluoromethyl)-imidazol-2-yl]-phenoxy]-2-propanol required as starting material may be prepared as follows:

(22a) At an internal temperature of 0°–50°, 10 g of potassium tert.-butoxide are added to a solution of 20 g of 2-(4-methoxyphenyl)-4-(trifluoromethyl)-1H-imidazole in 200 ml of dimethylformamide. After 20 minutes 10.7 ml of isopropyl iodide are added and the reaction mixture is subsequently stirred at room temperature. After 24 hours in each case, a further 10 g of potassium tert.-butoxide are added and then 10.7 ml of isopropyl iodide. In total, these measures are repeated three times. The total reaction period is 120 hours. Finally, the solvent is removed in a rotary evaporator, the residue is taken up in water and extracted several times with ethyl acetate. After evaporating off the organic phase, the residue is chromatographed on silica gel with ethyl acetate/hexane and 2-(4-methoxyphenyl)-1-isopropyl-4-(trifluoromethyl)-1H-imidazole is isolated from the main fractions in the form of a yellowish oil.

This product is used directly in the next step.

(22b) A solution of 15.5 g of 2-(4-methoxyphenyl)-1-(isopropyl)-4-(trifluoromethyl)-1H-imidazole in a mixture of 80 ml of glacial acetic acid and 80 ml of hydrobromic acid (48% strength) is heated under reflux for 24 hours. The solution is concentrated in a rotary evaporator to form a thick paste which is diluted with water, neutralised to pH 11 with concentrated ammonia and finally extracted several times with ethyl acetate. After drying the organic phase over magnesium sulphate and filtration, the filtrate is concentrated to a small volume in a rotary evaporator and hexane is added until crystallisation begins. 2-(4-hydroxyphenyl)-1-isopropyl-5-(trifluoromethyl)-1H-imidazole having a melting point of 249°–250° is obtained.

(22c) A suspension of 10 g of 2-(4-hydroxyphenyl)-1-isopropyl-4-(trifluoromethyl)-1H-imidazole and 10 g of anhydrous potassium carbonate in 100 ml of epichlorohydrin is heated under reflux for 35 minutes. The reaction mixture is cooled in an ice bath, filtered and the filtrate is concentrated in a rotary evaporator. The oil that remains behind is dissolved in ether, the solution is treated with active carbon, filtered and cooled in an ice/sodium chloride bath. On so doing, 2-[4-(2,3-epoxypropoxy)-phenyl]-1-isopropyl-4-(trifluoromethyl)-1H-imidazole crystallises out which, after filtration and drying, has a melting point of 98°–99°.

EXAMPLE 23

After the addition of 1 g of palladium-on-carbon catalyst (5%), a solution of 9.7 g of crude 1-[N-benzyl-2-(3-carbamoyl-4-hydroxyphenoxy)-ethylamino]-3-[4-[1-(2-hydroxyethyl)-4-(trifluoromethyl)-1H-imidazol-2-yl]-phenoxy]-2-propanol in 100 ml of methanol is hydrogenated under normal conditions until the absorption of hydrogen has ceased, the reaction product partly precipitating out of the solution. The suspension is diluted with 200 ml of dioxan/methanol 1:1, heated and filtered through a filter aid. The filtrate is freed of solvent in a rotary evaporator and the residue is recrystallised twice from methanol, yielding 1-[2-(3-carbamoyl-4-hydroxyphenoxy)-ethylamino]-3-[4-[1-(2-hydroxyethyl)-4-(trifluoromethyl)-1H-imidazol-2-yl]-phenoxy]-2-propanol having a melting point of 151°–153°.

The 1-[N-benzyl-2-(3-carbamoyl-4-hydroxyphenoxy)-ethylamino]-3-[4-[1-(2-hydroxyethyl)-4-(trifluoromethyl)-1H-imidazol-2-yl]-phenoxy]-2-propanol may be prepared as follows:

(23a) At an internal temperature of 0°–50°, 35.0 g of potassium tert.-butoxide are added to a solution of 35 g of 2-(4-methoxyphenyl)-4-(trifluoromethyl)-imidazole in 200 ml of dimethylformamide. After 20 minutes, a solution of 14.7 ml of 2-hydroxyethyl iodide in 100 ml of dimethylformamide is added dropwise within a period of 5 minutes, the mixture is then stirred for 120 hours at room temperature and the solvent is removed in a rotary evaporator; the residue is taken up in water and extracted several times with ethyl acetate. The organic phases are combined, the solvent is removed and the residue is chromatographed on silica gel with the solvent mixture ethyl acetate/hexane 1:1 and 1-(2-hydroxyethyl)-2-(4-methoxyphenyl)-4-(trifluoromethyl)-1H-imidazole is isolated from the main fractions in the form of a crystallising oil.

(23b) A solution of 14.6 g of 1-(2-hydroxyethyl)-2-(4-methoxyphenyl)-4-(trifluoromethyl)-1H-imidazole and 8.7 g of DL-methionine in 90 ml of methanesulphonic acid is stirred for 24 hours at 110°, then cooled, poured onto ice and the pH is adjusted to 10 with ammonia. The mixture is extracted several times with ethyl acetate, the combined organic phases are dried over sodium sulphate, filtered and the filtrate is concentrated to a small volume. 1-(2-hydroxyethyl)-2-(4-hydroxyphenyl)-4-(trifluoromethyl)-1H-imidazole having a melting point of 186°–188° can be obtained in crystalline form by the addition of hexane.

(23c) A suspension of 3.26 g of 1-(2-hydroxyethyl)-2-(4-hydroxyphenyl)-4-(trifluoromethyl)-1H-imidazole and 9.26 g of anhydrous potassium carbonate in 95 ml of epichlorohydrin is heated under reflux, while stirring, for 1 hour. The mixture is subsequently cooled in an ice bath, filtered and the filtrate freed of solvent in a rotary evaporator. The oil that remains behind is chromatographed on silica gel with ethyl acetate. The main fractions are combined and are caused to crystallise by the addition of hexane, yielding 2-[4-(2,3-epoxypropoxy)-phenyl]-1-(2-hydroxyethyl)-4-(trifluoromethyl)-1H-imidazole having a melting point of 110°–112°.

EXAMPLE 24

After the addition of 0.1 g of palladium-on-carbon catalyst (5%), a solution of 1.0 g of crude 1-[N-benzyl-2-(3-carbamoyl-4-benzyloxyphenoxy)-ethylamino]-3-[4-[1,4- or 1,5-dimethyl-1H-imidazol-2-yl]-phenoxy]-2-propanol in 10 ml of methanol is hydrogenated under normal conditions until the absorption of hydrogen has ceased, the catalyst is subsequently filtered off and the solvent removed in a rotary evaporator. The residue is recrystallised from a mixture of ethyl acetate/ether, yielding 1-[2-(3-carbamoyl-4-hydroxyphenoxy)-ethylamino]-3-[4-[1,4- or 1,5-dimethyl-1H-imidazol-2-yl]-phenoxy]-2-propanol in the form of an isomeric mixture in a ratio of approximately 1:1.

The 1-[N-benzyl-2-(3-carbamoyl-4-benzyloxyphenoxy)-ethylamino]-3-[4-[1,4- or 1,5-dimethyl-1H-imidazol-2-yl]-phenoxy]-2-propanol required as starting material may be prepared as follows:

(24a) A solution of 40 g of 5-[2-(benzylamino)-ethoxy]-0-benzylsalicylamide in 800 ml of methanol is stirred under reflux for 16 hours. The solution thus obtained, which contains 1-[N-benzyl-2-(3-carbamoyl-4-benzyloxyphenoxy)-ethylamino]-3-(4-benzaldehyde), is further processed as follows:

(24b) The reaction solution is diluted with a further 800 ml of methanol. 69.1 g of sodium acetate and 177 ml of methylglyoxal (30% in water) are then added and finally 270 ml of concentrated ammonia are added dropwise over a period of 15 minutes. After stirring for 5 days at room temperature, the solvent is extensively removed in a rotary evaporator, the residue is diluted with water and extracted with a large quantity of methylene chloride. The organic phase is evaporated to dryness and the residue is chromatographed on silica gel with a mixture of chloroform/methanol/ammonia (700:50:1). The main fractions are combined, the solvent is removed in a rotary evaporator and the crude 1-[N-benzyl-2-(3-carbamoyl-4-benzyloxyphenoxy)-ethylamino]-3-[4-[4-methyl-1H-imidazol-2-yl]-phenoxy]-2-propanol, which is obtained in the form of a yellowish foam, is dried thoroughly in a high vacuum and is used in that form in the next step.

(24c) 0.311 g of potassium tert.-butoxide is added to a solution of 1.6 g of 1-[N-benzyl-2-(3-carbamoyl-4-benzyloxyphenoxy)-ethylamino]-3-[4-[4-methyl-1H-imidazol-2-yl]-phenoxy]-2-propanol in 20 ml of dimethylformamide and, after 15 minutes, 0.487 g of methyl iodide is added dropwise thereto. After stirring for 3 hours at room temperature, the solvent is removed in a rotary evaporator and the residue is chromatographed on silica gel with the solvent mixture chloroform/methanol/ammonia (700:50:1). 1-[N-benzyl-2-(3-carbamoyl-4-benzyloxyphenoxy)-ethylamino]-3-[4-[1,4- or 1,5-dimethyl-1H-imidazol-2-yl]-phenoxy]-2-propanol is isolated from the main fractions as an isomeric mixture in the ratio of approximately 1:1 in the form of a brown oil which is used in that form in the next step.

EXAMPLE 25

After the addition of a total of 5 g of palladium-on-carbon catalyst (5%), a solution of 2.95 g of crude 1-[N-benzyl-2-(3-carbamoyl-4-hydroxyphenoxy)-ethylamino]-3-[4-[4-(trifluoromethyl)-thiazol-2-yl]-phenoxy]-2-propanol in 80 ml of methanol is hydrogenated at 60° and a pressure of 4 bar until the absorption of hydrogen has ceased, the reaction product partly precipitating out of the solution. The suspension is diluted with 50 ml of dioxan/methanol, heated and filtered through a filter aid. The filtrate is freed of solvent in a rotary evaporator and the residue is recrystallised twice from methanol, yielding 1-[2-(3-carbamoyl-4-hydroxyphenoxy)-ethylamino]-3-[4-[4-(trifluoromethyl)-thiazol-2-yl]-phenoxy]-2-propanol having a melting point of 202°-203°.

The 1-[N-benzyl-2-(3-carbamoyl-4-hydroxyphenoxy)-ethylamino]-3-[4-[4-(trifluoromethyl)-thiazol-2-yl]-phenoxy]-2-propanol used as starting material may be prepared as follows:

(25a) 12.6 g of 1-bromo-3,3,3-trifluoroacetone are added dropwise to a solution of 9.18 g of 4-hydroxythiobenzamide in 90 ml of ethanol, the mixture is stirred for 3 hours at room temperature, then 1 ml of concentrated sulphuric acid is added and the mixture is subsequently heated under reflux for 18 hours. The solvent is then removed in a rotary evaporator, the residue is diluted with ice water and the mixture is extracted with ethyl acetate. The combined organic phases are dried and concentrated to a small volume. The addition of hexane causes the crystallisation of 2-(4-hydroxyphenyl)-4-(trifluoromethyl)-thiazole having a melting point of 161°-162°.

(25b) A mixture of 5 ml of epichlorohydrin and 0.5 g of potassium carbonate is heated under reflux. 0.5 g of 2-(4-hydroxyphenyl)-4-(trifluoromethyl)-thiazole is added in one portion and the reaction mixture is then heated under reflux for a further 15 minutes. After cooling, the mixture is filtered, the filtrate is concentrated by evaporation in a rotary evaporator and the residue is taken up in 6 ml of dichloromethane; 100 mg of tetrabutylammonium hydrogen sulphate and 6 ml of 2N sodium hydroxide solution are added to the solution and the whole is stirred for 3 hours at room temperature. The organic phase is separated off, washed and dried and finally the solvent is removed in a rotary evaporator. The residue is crystallised from ether/hexane yielding 2-[4-(2,3-epoxypropoxy)-phenyl]-4-(trifluoromethyl)-thiazole having a melting point of 97°-98°.

(25c) A solution of 7.0 g of 2-[4-(2,3-epoxypropoxy)-phenyl]-4-(trifluoromethyl)-thiazole and 6.01 g of 5-[2-(benzylamino)-ethoxy]-salicylamide in 150 ml of isopropanol is heated under reflux for 18 hours and the solvent is subsequently removed in a rotary evaporator. The 1-[N-benzyl-2-(3-carbamoyl-4-hydroxyphenoxy)-ethylamino]-3-[4-[4-(trifluoromethyl)-thiazol-2-yl]-phenoxy]-2-propanol, obtained in the form of an oil, is further processed in that form.

EXAMPLE 26

After the addition of 0.69 g of palladium-on-carbon catalyst (10%), a solution of 3.0 g of crude 1-[N-benzyl-2-(3-carbamoyl-4-hydroxyphenoxy)-ethylamino]-3-[4-(thiazol-2-yl)-phenoxy]-2-propanol in a mixture of 30 ml of glacial acetic acid and 3 ml of trifluoroacetic acid is hydrogenated at 45° and normal pressure until the absorption of hydrogen has ceased. The suspension is filtered through a filter aid and the filtrate is freed of solvent; ice water is added to the residue, the pH is adjusted to approximately 9 with ammonia and extraction is carried out several times with ethyl acetate. The combined organic phases are dried over sodium sulphate, concentrated by evaporation and the residue is recrystallised from isopropanol, yielding 1-[2-(3-carbamoyl-4-hydroxyphenoxy)-ethylamino]-3-[4-(thiazol-2-yl)-phenoxy]-2-propanol having a melting point of 136°-138°.

The 1-[N-benzyl-2-(3-carbamoyl-4-hydroxyphenoxy)-ethylamino]-3-[4-(thiazol-2-yl)-phenoxy]-2-propanol used as starting material may be prepared as follows:

(26a) 0.5 g of 2-(4-hydroxyphenyl)-thiazole is added in one portion to a mixture, heated under reflux, of 5 ml of epichlorohydrin and 0.79 g of potassium carbonate and the reaction mixture is then heated under reflux for a further 20 minutes. After cooling, the mixture is filtered, the filtrate is concentrated by evaporation in a rotary evaporator and the residue is dissolved in 6 ml of dichloromethane; 100 mg of tetrabutylammonium hydrogen sulphate and 6 ml of 2N sodium hydroxide solution are added to the solution and the whole is stirred for 3 hours at room temperature. The organic phase is separated off, washed with water and dried over sodium sulphate and the solvent is then removed in a rotary evaporator. The residue is recrystallised from a mixture of ether/hexane, yielding 2-[4-(2,3-epoxypropoxy)-phenyl]-thiazole having a melting point of 82°–93°.

(26b) A solution of 6.50 g of 2-[4-(2,3-epoxypropoxy)-phenyl]-thiazole and 7.25 g of 5-[2-(benzylamino)-ethoxy]-salicylamide in 150 ml of isopropanol is heated under reflux for 18 hours and the solvent is subsequently removed in a rotary evaporator. The 1-[N-benzyl-2-(3-carbamoyl-4-hydroxyphenoxy)-ethylamino]-3-[4-(thiazol-2-yl)-phenoxy]-2-propanol, obtained in the form of an oil, is further processed in that form.

EXAMPLE 27

4.28 ml of 5.9N methanolic hydrochloric acid are added to a solution of 8.39 g of 1-amino-3-[4-(1-methyl-4-(trifluoromethyl)-1H-imidazol-2-yl)-phenoxy]-2-propanol in 250 ml of methanol. The pH is adjusted to 8–9 by the addition of solid potassium hydroxide; there are subsequently added 25 g of molecular sieve (pore size 3 Å), 5.6 g of 2,3-dihydro-2,2-dimethyl-7-(2-oxoethoxy)-4H-1,3-benzoxazin-4-one and finally 0.59 g of sodium cyanoborohydride. The mixture, containing the corresponding Schiff's base, is stirred under reflux at room temperature for 18 hours and, after the addition of 50 ml of 5.9N methanolic hydrochloric acid, for a further one hour, filtered and the solvent is removed in a rotary evaporator. The residue is chromatographed on silica gel with a mixture of chloroform/methanol/ammonia (40:50:5), the main fractions are freed of solvent and the residue is recrystallised from methanol, yielding 1-[2-(3-carbamoyl-4-hydroxyphenoxy)-ethylamino]-3-[4-[1-methyl-4-(trifluoromethyl)-1H-imidazol-2-yl]-phenoxy]-2-propanol having a melting point of 195°–197°.

EXAMPLE 28

0.48 g of potassium tert.-butoxide is added while stirring in an ice bath to a solution of 1 g of the 1-[2-(3-carbamoyl-4-hydroxyphenoxy)-ethylamino]-3-[4-[4-(trifluoromethyl)-1H-imidazol-2-yl]-phenoxy]-2-propanol obtained according to Example 3 in 20 ml of dimethylformamide. After 10 minutes, a solution of 0.3 g of methyl iodide in 1 ml of dimethylformamide is added dropwise over a period of 20 minutes. The mixture is then stirred for 2 hours at room temperature, the solvent is removed in a rotary evaporator and the residue is chromatographed on silica gel with a solvent mixture of chloroform/methanol/ammonia (700:50:1), yielding the two isomeric compounds 1-[2-(3-carbamoyl-4-hydroxyphenoxy)-ethylamino]-3-[4-[1-methyl-4-(trifluoromethyl)-1H-imidazol-2-yl]-phenoxy]-2-propanol having a melting point of 195°–197° and 1-[2-(3-carbamoyl-4-hydroxyphenoxy)-ethylamino]-3-[4-[1-methyl-5-(trifluoromethyl)-1H-imidazol-2-yl]-phenoxy]-2-propanol having a melting point of 157°–159°.

The described methylation may also be carried out by means of diazomethane in the following manner:

An excess of an ethereal diazomethane solution is added to a solution of 1 g of 1-[2-(3-carbamoyl-4-hydroxyphenoxy)-ethylamino]-3-[4-[4-(trifluoromethyl)-1H-imidazol-2-yl]-phenoxy]-2-propanol in 30 ml of methanol and the mixture is stirred for one hour at room temperature.

The reaction solution is worked up and chromatographed as described above and the two isomeric end products identified above are obtained.

EXAMPLE 29

A solution of 5.2 g of 1-[4-(1,6-dihydro-1-methyl-6-oxo-2-pyridyl)-phenoxy]-3-[2-(3-carbamoyl-4-hydroxyphenoxy)-N-benzylethylamino]-2-propanol in 100 ml of methanol is hydrogenated under normal conditions in the presence of 1 g of palladium-on-carbon catalyst (5%). The hydrogenated mixture is filtered with suction, the filtrate is concentrated to dryness by evaporation and the residue is washed with ethyl acetate. Recrystallisation from isopropanol yields pure 1-[4-(1,6-dihydro-1-methyl-6-oxo-2-pyridyl)-phenoxy]-3-[2-(3-carbamoyl-4-hydroxyphenoxy)-ethylamino]-2-propanol having a melting point of 148°–150°.

The N-benzyl compound required as starting material may be prepared as follows:

(29a) A mixture of 5.54 g of 6-(4-benzyloxyphenyl)-α-pyridone (J. Thesing and A. Müller, Chem. Ber. 1957, 711) having a melting point of 210°–212°, 4.2 g of potassium carbonate and 2 ml of methyl iodide in 40 ml of dimethylformamide is stirred for 48 hours at room temperature. The solvent is distilled off in vacuo and the residue is stirred with 190 ml of methylene chloride. The inorganic portions are separated off and the filtrate is concentrated to dryness by evaporation. A light brown powder remains to which 0.5 ml of methyl iodide is added and the whole is heated for 13 hours in a pressure tube at a bath temperature of 150°. The reaction mass is dissolved in 100 ml of methylene chloride, washed in succession with water and saturated aqueous sodium chloride solution, dried over sodium sulphate and the solvent is distilled off. The residue is recrystallised from 80 ml of ethyl acetate, yielding 6-(4-benzyloxyphenyl)-1-methyl-α-pyridone having a melting point of 167°–170°.

(29b) A solution of 18.4 g of 6-(4-benzyloxyphenyl)-1-methyl-α-pyridone in 550 ml of methanol is hydrogenated in the presence of 10 g of palladium-on-carbon catalyst (5%), the hydrogenated mixture is filtered off from the catalyst and washed with methanol. After concentration, 6-(4-hydroxyphenyl)-1-methyl-α-pyridone having a melting point of 236°–238° crystallises out of the methanolic solution.

(29c) A mixture of 6.35 g of the substance obtained according to Example (29b), 63 ml of epichlorohydrin and 8.7 g of potassium carbonate is heated for 2 hours at a bath temperature of 125°. The reaction mixture is then diluted with methylene chloride, filtered with suction and the filtrate is concentrated to dryness by evaporation. The oil/crystal mixture that remains is recrystallised from 10 ml of dimethoxyethane, yielding 3-[4-(1-methyl-2-oxodihydropyridin-6-yl)-phenoxy]-1,2-epoxipropane.

(29d) A mixture of 3.8 g of the epoxide obtained according to Example (29c) and 4.3 g of 5-[2-(benzylamino)-ethoxy]-salicylamide in 31 ml of isopropanol is heated at a bath temperature of 90°. From the original solution a suspension is produced which, after 4 hours, is cooled and filtered with suction. The resulting crystals are recrystallised from 40 ml of methylcellosolve, yielding 1-[N-benzyl-2-(3-carbamoyl-4-hydroxyphenoxy)-ethylamino]-3-[4-(1-methyl-2-oxodihydropyridin-6-yl)-phenoxy]-2-propanol having a melting point of 177°–179°.

EXAMPLE 30

A solution of 1.35 g of 1-[4-(3,4-dihydro-3,6-dimethyl-4-oxo-2-pyrimidinyloxy)-phenoxy]-3-[2-(3-carbamoyl-4-hydroxyphenoxy)-N-benzylaminoethyl]-2-propanol in 20 ml of methanol is hydrogenated under normal conditions in the presence of 0.3 g of palladium-on-carbon catalyst (5%). For working up, the warm reaction mixture is filtered with suction, washed with warm methanol and the filtrate is concentrated by evaporation. 45 ml of isopropanol are added to the residue, the whole is stirred for 1 hour and an amorphous precipitate is filtered off. The pH of the filtrate is adjusted to ~1 with 3N ethereal hydrogen chloride solution and 1-[4-(3,4-dihydro-3,6-dimethyl-4-oxo-2-pyrimidinyloxy)-phenoxy]-3-[2-(3-carbamoyl-4-hydroxyphenoxy)-ethylamino]-2-propanol precipitates out in the form of the hydrochloride. After recrystallisation from methanol, the product is dried for 18 hours at 80° and 0.1 mm Hg; it has a melting point of 174°–176° (evolution of gas); the compound contains water of crystallisation.

The N-benzyl compound required as starting material may be prepared as follows:

(30a) 20 mg of sodium methoxide are added to a solution of 3.5 g of 4-benzyloxy-N-methylbenzamidine in 35 ml of acetoacetic ester and the mixture is stirred for 17 hours at a bath temperature of 100°. The resulting brown solution is concentrated by evaporation in vacuo and the residue is dissolved in ethyl acetate. This solution is washed in succession with 0.5N sodium hydroxide solution, water, then with aqueous saturated sodium chloride solution, and the organic phase is dried over sodium sulphate and concentrated by evaporation. The residue is chromatographed over silica gel (methylene chloride/methanol 99:1), yielding crystalline 2-(4-benzyloxyphenyl)-1,4-dimethyl-1H-pyrimidin-6-one.

(30b) A solution of 1.8 g of the compound obtained according to Example (30a) in 20 ml of methanol is hydrogenated under normal conditions in the presence of 0.3 g of palladium-on-carbon catalyst (5%). The crystalline product obtained after working up is recrystallised from methylcellosolve and yields 2-(4-hydroxyphenyl)-1,4-dimethyl-1H-pyrimidin-6-one having a melting point of approximately 260°.

(30c) A mixture of 0.6 g of the compound obtained according to Example (30b) with 10 ml of epichlorohydrin and 0.58 g of potassium carbonate is stirred for 1 hour at a bath temperature of 130°. After working up, 1-[4-(3,4-dihydro-3,6-dimethyl-4-oxo-2-pyrimidinyloxy)-phenoxy]-2,3-epoxipropane is obtained in the form of a yellow viscous oil.

(30d) 0.9 g of the resulting crude product in 5 ml of isopropanol is stirred for 7 hours with 0.87 g of 5-[2-(benzylamino)-ethoxy]-salicylamide at a bath temperature of 95°. The mixture is then diluted with 10 ml of isopropanol and 1.5 ml of 3N ethereal hydrogen chloride solution are added. Decanting from the sticky precipitate formed is carried out and this precipitate is treated with aqueous potassium bicarbonate solution and ethyl acetate. After working up, there is obtained from the organic phase 1-[4-(3,4-dihydro-3,6-dimethyl-4-oxo-2-pyrimidinyloxy)-phenoxy]-3-[2-(3-carbamoyl-4-hydroxyphenoxy)-N-benzylaminoethyl]-2-propanol which is further processed in that form.

EXAMPLE 31

0.8 g of 1-amino-3-[4-(1-methyl-4-(trifluoromethyl)-1H-imidazol-2-yl)-phenoxy]-2-propanol and 0.6 g of 5-(2-oxopropoxy)-salicylamide are dissolved in 20 ml of methanol. After the addition of 1 drop of concentrated sulphuric acid and 0.2 g of platinium-on-carbon catalyst (10%), the solution, which contains the corresponding Schiff's base that is formed, is hydrogenated until the absorption of hydrogen (1 molar equivalent) has ceased. The catalyst is filtered off and the filtrate is concentrated by evaporation. The brownish oil that remains is 1-[2-(3-carbamoyl-4-hydroxyphenoxy)-1-methylethylamino]-3-[4-(1-methyl-4-(trifluoromethyl)-1H-imidazol-2-yl)-phenoxy]-2-propanol in the form of a diastereoisomeric mixture. It has a proton NMR spectrum that is consistent with the supposed structure (100 MHz, DMSO-$d_6$).

EXAMPLE 32

A solution of 4.5 g of the sodium salt of 1-[2-(3-carboxy-4-hydroxyphenoxy)-ethylamino]-3-[4-[1-methyl-4-(trifluoromethyl)-1H-imidazol-2-yl]-phenoxy]-2-propanol in 50 ml of 1N methanolic hydrochloric acid is heated under reflux for 48 hours. The reaction mixture is cooled, the sodium chloride is filtered off and the filtrate is freed of solvent in a rotary evaporator. The residue, which is the corresponding methyl ester, is treated twice with methanol which is then evaporated off, and the residue is taken up in 20 ml of dioxan; 50 ml of concentrated aqueous ammonia is added to the solution and the mixture is stirred for 40 hours at room temperature. After evaporating off the solvent in a rotary evaporator, the residue is stirred with water, the precipitate is filtered off and, after drying, is recrystallised from methanol, yielding 1-[2-(3-carbamoyl-4-hydroxyphenoxy)-ethylamino]-3-[4-[1-methyl-4-(trifluoromethyl)-1H-imidazol-2-yl]-phenoxy]-2-propanol having a melting point of 195°–197°.

The sodium salt of 1-[2-(3-carboxy-4-hydroxyphenoxy)-ethylamino]-3-[4-(trifluoromethyl)-1H-imidazol-2-yl]-phenoxy]-2-propanol required as starting material may be obtained as follows:

A solution of 5.0 g of 1-[2-(3-carbamoyl-4-hydroxyphenoxy)-ethylamino]-3-[4-[1-methyl-4-(trifluoromethyl)-1H-imidazol-2-yl]-phenoxy]-2-propanol in 75 ml of 1N sodium hydroxide solution is stirred under reflux for 20 hours under nitrogen. The solution is cooled, the salt that precipitates out is filtered off and recrystallised from water. After drying at 80° in a high vacuum, the sodium salt of 1-[2-(3-carboxy-4-hydroxyphenoxy)-ethylamino]-3-[4-[1-methyl-4-(trifluoromethyl)-1H-imidazol-2yl]-phenoxy]-2-propanol having a melting point of 236°–238° is obtained.

EXAMPLE 33

A solution of 1.35 g of 1-[N-benzyl-2-(3-carbamoyl-4-hydroxyphenoxy)-ethylamino]-3-[4-(1,4-dimethyl-1H-pyrimidin-6-on-2-yl)-phenoxy]-2-propanol in 20 ml of methanol is hydrogenated under normal conditions in the presence of 0.3 g of palladium-on-carbon catalyst (5%). For working up, the warm reaction mixture is filtered off from the catalyst with suction, the filter residue is washed with warm methanol and the filtrate is concentrated by evaporation. 45 ml of isopropanol are added to the residue, the mixture is stirred for 1 hour and an amorphous precipitate is filtered off. The pH of the filtrate is adjusted to 1 with 3N a ethereal hydrochloric acid, whereupon a precipitate is formed which is recrystallised from methanol. 1-[2-(3-carbamoyl-4-hydroxyphenoxy)-ethylamino]-3-[4-(1,4-dimethyl-1H-pyrimidin-6-on-2-yl)-phenoxy]-2-propanol hydrochloride is obtained in the form of a semihydrate.

After drying for 18 hours at 100° and 0.1 mm Hg, the compound has a melting point of 160°–162° (evolution of gas). The substance is hygroscopic.

EXAMPLE 34

Analogously to Example 12, 19.5 g of 3-[4-(2,3-epoxypropoxy)-phenyl]-4-methyl-5-methylthio-4H-1,2,4-triazole are reacted with 11.0 g of 5-(2-aminoethoxy)-salicylamide in 70 ml of dimethyl sulphoxide. The resin-like crude product that is obtained on mixing with water is extracted by boiling with dioxan, the dioxan solution is concentrated by evaporation and the residue is recrystallised from methanol. 1-[2-(3-carbamoyl-4-hydroxyphenoxy)-ethylamino]-3-[4-(4-methyl-5-methylthio-4H-1,2,4-triazol-3-yl)-phenoxy]-2-propanol having a melting point of 123°–125° is obtained.

The starting material may be prepared in the following manner:

(34a) 30.4 g of 3-(4-methoxyphenyl)-4-methyl-5-methylthio-4H-1,2,4-triazole and 38.5 g of D,L-methionine in 230 ml of methanesulphonic acid are heated for 20 hours at 110°–120°. After working up analogously to Example (15b), 3-(4-hydroxyphenyl)-4-methyl-5-methylthio-4H-1,2,4-triazole having a melting point of 207°–210° (from isopropanol) is obtained.

(34b) A mixture of 18.5 g of the compound obtained according to (34a), 90 g of potassium carbonate and 21 ml of epichlorohydrin in 1 liter of acetone is stirred under reflux for 24–30 hours. After filtration and concentration by evaporation of the filtrate, crude 3-[4-(2,3-epoxypropoxy)-phenyl]-4-methyl-5-methylthio-4H-1,2,4-triazole is obtained in the form of an oil which is further used in that form.

Chromatographing a sample on silica gel and elution with chloroform to which 1% methanol is added yields the compound in pure form as crystals having a melting point of 129°–131°.

EXAMPLE 35

Solutions of 5.0 g of crude 1,5-dimethyl-2-[3-(2,3-epoxypropoxy)-phenyl]-pyrrole in 15 ml of isopropanol and of 3.0 g of 5-(2-aminoethoxy)-salicylamide in 30 ml of isopropanol are combined and boiled under reflux for 2.5 hours. A portion of the precipitated reaction product is dissolved by the addition of 50 ml of methanol. The filtered solution is evaporated to dryness and the residue is recrystallised twice from ethyl acetate, yielding 1-[2-(3-carbamoyl-4-hydroxyphenoxy)-ethylamino]-3-[3-(1,5-dimethylpyrrol-2-yl)-phenoxy]-2-propanol having a melting point of 108°–112°.

(35a) At approximately 40°, to a solution of 2.5 g of potassium cyanide in 250 ml of dimethylformamide there are added dropwise, while stirring, first of all a solution of 106 g of 3-benzyloxybenzaldehyde in 250 ml of dimethylformamide and then a solution of 26.5 g of 1-buten-3-one in 500 ml of dimethylformamide. After the addition has been completed, stirring is continued for a further 2–3 hours at 40°, the reaction mixture is poured into 3 liters of water and extracted 3 times using 500 ml of chloroform each time. The combined chloroform extracts are washed in succession with 250 ml in each case of water, 0.5N hydrochloric acid and saturated sodium bicarbonate solution, dried over magnesium sulphate and concentrated by evaporation, yielding crude 1-(3-benzyloxy)-1,4-pentanedione in the form of a dark oil which is processed without further purification.

(35b) 25 g of methyl aminoacetate are added to a solution of 56 g of the resulting crude 1-(3-benzyloxy)-1,4-pentanedione in 200 ml of glacial acetic acid and the mixture is boiled under reflux for 24 hours. After concentration by evaporation there remains a dark red oil which is dissolved in ether and washed in succession with 50 ml in each case of water, 2N sodium hydroxide solution, water and saturated aqueous sodium chloride solution. After drying and concentration by evaporation, 2-(3-benzyloxyphenyl)-1,5-dimethylpyrrole is obtained in the form of a brown oil which is further used in crude form.

(35c) 35.7 g of the crude compound obtained according to (35b) in a mixture of 250 ml of methanol and 250 ml of tetrahydrofuran are hydrogenated in the presence of 8 g of palladium-on-carbon catalyst (5%). After 1 molar equivalent of hydrogen has been absorbed the hydrogenation ceases. After filtering off the catalyst and evaporating off the solvent, crude 1,5-dimethyl-2-(3-hydroxyphenyl)-pyrrole is obtained in the form of a brown oil.

(35d) While stirring, a mixture of 10 g of the resulting crude 1,5-dimethyl-2-(3-hydroxyphenyl)-pyrrole, 50 ml of epichlorohydrin and 15.2 g of potassium carbonate is heated at boiling point for 3 hours. The reaction mixture is cooled, filtered and concentrated by evaporation. The residue is divided between 200 ml of ether and 20 ml of 2N sodium hydroxide solution; the ether phase is separated off, dried over magnesium sulphate and concentrated by evaporation. The crude 1,5-dimethyl-2-[3-(2,3-epoxypropoxy)-phenyl]-pyrrole is obtained in the form of an oil and is further used in that form.

EXAMPLE 36

Analogously to the procedures described in the preceding examples it is possible to prepare the following compounds, or N-oxides or salts thereof, especially pharmaceutically acceptable, non-toxic acid addition salts:

1-[2-(3-Carbamoyl-4-hydroxyphenoxy)-ethylamino]-3-[4-(1-methyl-3-trifluoromethyl-1H-1,2,4-triazol-5-yl)-phenoxy]-2-propanol;

1-[2-(3-Carbamoyl-4-hydroxyphenoxy)-ethylamino]-3-[4-(1-methyl-1H-1,2,4-triazol-3-yl)-phenoxy]-2-propanol;

1-[2-(3-Carbamoyl-4-hydroxyphenoxy)-ethylamino]-3-[4-(1-methyl-4H-1,2,4-triazol-3-yl)-phenoxy]-2-propanol;

1-[2-(3-Carbamoyl-4-hydroxyphenoxy)-ethylamino]-3-[4-(1-methyl-5-methylsulphonyl-1H-1,2,4-triazol-3-yl)-phenoxy]-2-propanol;

1-[2-(3-Carbamoyl-4-hydroxyphenoxy)-ethylamino]-3-[4-(3-n-butyl-1-methyl-1H-1,2,4-triazol-5-yl)-phenoxy]-2-propanol;

1-[2-(3-Carbamoyl-4-hydroxyphenoxy)-ethylamino]-3-[4-(5-carbamoyl-1-methyl-1H-1,2,4-triazol-3-yl)-phenoxy]-2-propanol;

1-[2-(3-Carbamoyl-4-hydroxyphenoxy)-ethylamino]-3-[4-(5-trifluoromethyl-1,3,4-oxadiazol-2-yl)-phenoxy]-2-propanol;

1-[2-(3-Carbamoyl-4-hydroxyphenoxy)-ethylamino]-3-[4-(4-methyl-5-methylsulphonyl-4H-1,2,4-triazol-3-yl)-phenoxy]-2-propanol;

1-[2-(3-Carbamoyl-4-hydroxyphenoxy)-ethylamino]-3-[4-(3-cyanopyridin-6-yl)-phenoxy]-2-propanol.

EXAMPLE 37

Tablets containing 20 mg of active substance and having the following composition are manufactured in the customary manner:

| Composition: | |
|---|---|
| 1-[2-(3-Carbamoyl-4-hydroxyphenoxy)-ethylamino]-3-[4-(1-methyl-4-(trifluoromethyl)-1H—imidazol-2-yl)-phenoxy]-2-propanol monomethanesulphonate | 20 mg |
| wheat starch | 60 mg |
| lactose | 50 mg |
| colloidal silica | 5 mg |
| talc | 9 mg |
| magnesium stearate | 1 mg |
| | 145 mg |

Preparation

1-[2-(3-carbamoyl-4-hydroxyphenoxy)-ethylamino]-3-[4-[1-methyl-4-(trifluoromethyl)-1H-imidazol-2-yl]-phenoxy]-2-propanol monomethanesulphonate is mixed with a portion of the wheat starch and with the lactose and colloidal silica, and the mixture is forced through a sieve. On a water bath, a further portion of the wheat starch is made into a paste with 5 times the quantity of water and the powder mixture is kneaded with this until a slightly plastic mass has been produced.

The plastic mass is pressed through a sieve of approximately 3 mm mesh width, dried and the resulting dry granulate is again forced through a sieve. The remaining wheat starch, the talc and the magnesium stearate are then mixed in and the mixture is pressed into tablets that weigh 145 mg and have a breaking notch.

EXAMPLE 38

Tablets containing 1 mg of active substance and having the following composition are manufactured in the customary manner:

| Composition: | |
|---|---|
| 1-[2-(3-Carbamoyl-4-hydroxyphenoxy)-ethylamino]-3-[4-[1-methyl-4-(trifluoromethyl)-1H—imidazol-2-yl]-phenoxy]-2-propanol monomethanesulphonate | 1 mg |
| wheat starch | 60 mg |
| lactose | 50 mg |
| colloidal silica | 5 mg |
| talc | 9 mg |
| magnesium stearate | 1 mg |
| | 126 mg |

Preparation

1-[2-(3-carbamoyl-4-hydroxyphenoxy)-ethylamino]-3-[4-[1-methyl-4-(trifluoromethyl)-1H-imidazol-2-yl]-phenoxy]-2-propanol monomethanesulphonate is mixed with a portion of the wheat starch and with the lactose and colloidal silica, and the mixture is forced through a sieve. On a water bath, a further portion of the wheat starch is made into a paste with 5 times the quantity of water and the powder mixture is kneaded with this until a slightly plastic mass has been produced.

The plastic mass is pressed through a sieve of approximately 3 mm mesh width, dried and the resulting dry granulate is again forced through a sieve. The remaining wheat starch, the talc and the magnesium stearate are then mixed in and the mixture is pressed into tablets that weigh 145 mg and have a breaking notch.

EXAMPLE 39

Capsules containing 10 mg of active substance are manufactured in the customary manner as follows:

| Composition: | |
|---|---|
| 1-[2-(3-carbamoyl-4-hydroxyphenoxy)-ethylamino]-3-[4-[1-methyl-4-(trifluoromethyl)-1H—imidazol-2-yl]-phenoxy]-2-propanol monomethanesulphonate | 2500 mg |
| talc | 200 mg |
| colloidal silica | 50 mg |

Preparation

The active substance is intimately mixed with the talc and the collidal silica, the mixture is forced through a sieve of 0.5 mm mesh width and is then introduced, in 11 mg portions, into hard gelatin capsules of suitable size.

EXAMPLE 40

A sterile solution of 5.0 g of 1-[2-(3-carbamoyl-4-hydroxyphenoxy)-ethylamino]-3-[4-[1-methyl-4-(trifluoromethyl)-1H-imidazol-2-yl]-phenoxy]-2-propanol monomethanesulphonate in 5000 ml of distilled water is introduced into 5 ml ampoules, which contain 5 mg of active substance in 5 ml of solution.

EXAMPLE 41

With the addition of 100.0 ml of 0.10N hydrochloric acid, 3.62 g of 1-[2-(3-carbamoyl-4-hydroxyphenoxy)-ethylamino]-3-[4-[1-methyl-(4-trifluoromethyl)-1H-imidazol-2-yl]-phenoxy]-2-propanol are dissolved with 18,000 ml of distilled water to make up a volume of 18,100 ml. The sterilised solution is introduced into 5 ml ampoules, which contain 1 mg of active substance.

EXAMPLE 42

Instead of the compound used as active substance in Examples 37 to 41, it is also possible to use the following compounds of the formula I, or pharmaceutically acceptable, non-toxic acid addition salts thereof, as active substances in tablets, dragees, capsules, ampoule solutions and so on:

1[2-(3-carbamoyl-4-hydroxyphenoxy)-ethylamino]-3-[4-[5-[4-(trifluoromethyl)-1H-imidazol-2-yl]-2-furyl]-phennoxy]-2-propanol, 1-[2-(3-carbamoyl-4-hydroxyphenoxy)-ethylamino]-3-[4-[4-(trifluoromethyl)-1H-imidazol-2-yl]-phenoxy]-2-propanol, 1-[2-(3-carbamoyl-4-hydroxyphenoxy)-ethylamino]-3-[4-[4-methyl-6-(trifluoromethyl)-pyrimidin-2-yl]-phenoxy]-2-propanol, 1-[2-(3-carbamoyl-4-hydroxyphenoxy)-ethylamino]-3-[4-(4,6-dimethylpyrimidin-2-yl)-phenoxy]-2-propanol, 1-[2-(3-carbamoyl-4-hydroxyphenoxy)-ethylamino]-3-[4-(3,5-dicarboethoxy-2,6-dimethylpyridin-4-yl)-phenoxy]-2-propanol, 1-[2-(3-carbamoyl-4-hydroxyphenoxy)-ethylamino]-3-(4-biphenyloxy)-2-propanol, 1-[2-(3-carbamoyl-4-hydroxyphenoxy)-ethylamino]-3-

[4-(1-methyl-1H-imidazol-2-yl)-phenoxy]-2-propanol, 1-[2-(4-carbamoyl-3-hydroxyphenoxy)-ethylamino]-3-[4-[1-methyl-4-(trifluoromethyl)-1H-imidazol-2-yl]-phenoxy]-2-propanol, 1-[2-(3-carbamoyl-4-hydroxyphenoxy)-ethylamino]-3-[4-(4-acetyl-1,5-dimethyl-1H-imidazol-2-yl)-phenoxy]-2-propanol, 1-[2-(3-carbamoyl-4-hydroxyphenoxy)-ethylamino]-3-[4-(1-methyl-3-methylthio-1H-1,2,4-triazol-5-yl)-phenoxy]-2-propanol, 1-[2-(3-carbamoyl-4-hydroxyphenoxy)-ethylamino]-3-[2-(indol-2-yl)-phenoxy]-2-propanol, 1-[2-(3-carbamoyl-4-hydroxyphenoxy)-ethylamino]-3-[4-(1,4,5-trimethyl-1H-imidazol-2-yl)-phenoxy]-2-propanol, 1-[2-(3-carbamoyl-4-hydroxyphenoxy)-ethylamino]-3-[4-(4-methyl-5-trifluoromethyl-4H-1,2,4-triazol-3-yl)-phenoxy]-2-propanol, 1-[2-(3-carbamoyl-4-hydroxyphenoxy)-ethylamino]-3-[4-(1-methyl-5-(trifluoromethyl)-1H-1,2,4-triazol-3-yl)-phenoxy]-2-propanol, 1-[2-(3-carbamoyl-4-hydroxyphenoxy)-ethylamino]-3-[4-(1-methyl-3-methylsulphonyl-1H-1,2,4-triazol-5-yl)-phenoxy]-2-propanol, 1-[2-(3-carbamoyl-4-hydroxyphenoxy)-ethylamino]-3-[4-(2-methyl-2H-tetrazol-5-yl)-phenoxy]-2-propanol, 1-[2-(3-carbamoyl-4-hydroxyphenoxy)-ethylamino]-3-[4-[1-methyl-5-(trifluoromethyl)-1H-imidazol-2-yl]-phenoxy]-2-propanol, 1-[2-(3-carbamoyl-4-hydroxyphenoxy)-ethylamino]-3-[4-[1-isopropyl-4-(trifluoromethyl)-1H-imidazol-2-yl]-phenoxy]-2-propanol, 1-[2-(3-carbamoyl-4-hydroxyphenoxy)-ethylamino]-3-[4-[1-(2-hydroxyethyl)-4-(trifluoromethyl)-1H-imidazol-2-yl]-phenoxy]-2-propanol, 1-[2-(3-carbamoyl-4-hydroxyphenoxy)-ethylamino]-3-[4-[1,4-or 1,5-dimethyl-1H-imidazol-2-yl]-phenoxy]-2-propanol in the form of an isomeric mixture in a ratio of approximately 1:1, 1-[2-(3-carbamoyl-4-hydroxyphenoxy)-ethylamino]-3-[4-[4-(trifluoromethyl)-thiazol-2-yl]-phenoxy]-2-propanol, 1-[2-(3-carbamoyl-4-hydroxyphenoxy)-ethylamino]-3-[4-(thiazol-2-yl)-phenoxy]-2-propanol, 1-[2-(3-carbamoyl-4-hydroxyphenoxy)-1-methylethylamino]-3-[4-(1-methyl-4-(trifluoromethyl)-1H-imidazol-2-yl)-phenoxy]-2-propanol, 1-[4-(1,6-dihydro-1-methyl-6-oxo-2-pyridinyloxy)-phenoxy]-3-[2-(3-carbamoyl-4-hydroxyphenoxy)-ethylamino]-2-propanol, 1-[4-(3,4-dihydro-3,6-dimethyl-4-oxo-2-pyrimidinyloxy)-phenoxy]-3-[2-(3-carbamoyl-4-hydroxyphenoxy)-ethylamino]-2-propanol, 1-[2-(3-carbamoyl-4-hydroxphenoxy)-ethylamino]-3-[4-(1,4-dimethyl-1H-pyrimidin-6-on-2-yl)-phenoxy]-2-propanol, 1-[2-(3-carbamoyl-4-hydroxyphenoxy)-ethylamino]-3-[4-(4-methyl-5-methylthio-4H-1,2,4-triazol-3-yl)-phenoxy]-2-propanol, or 1-[2-(3-carbamoyl-4-hydroxyphenoxy)-ethylamino]-3-[3-(1,5-dimethylpyrrol-2-yl)-phenoxy]-2-propanol.

What is claimed is:
1. A compound of the formula

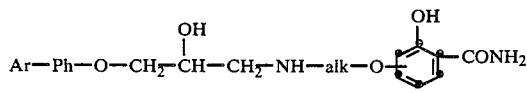

in which:
Ar represents pyrrolyl, imidazolyl, triazolyl, pyridyl, or dihydro-6-oxo-pyridyl substituted by lower alkyl, hydroxy lower alkyl, halo lower alkyl, lower alkylthio, lower alkylsulphonyl, lower alkanoyl and lower alkoxy carbonyl;
Ph represents 1,4-phenylene optionally substituted by lower alkyl or halogen;
alk represents an alkylene radical having 2 or 3 carbon atoms, the adjacent nitrogem atom and the adjacent oxygen atom being separated from each other by 2 or 3 carbon atoms; and the N-oxides or salts thereof.

2. 1-[2-(3-carbamoyl-4-hydroxyphenoxy)-ethylamino]-3-8 4-[1-methyl-4-(trifluoromethyl)-1H-imidazol-2-yl]-phenoxy]-2-propanol, in the form of a racemate, an optical antipode or a pharmaceutically acceptable non-toxic acid addition salt thereof.

3. 1-[2-(3-carbamoyl-4-hydroxyphenoxy)-ethylamino]-3-[4-[1-methyl-1H-imidazol-2-yl]-phenoxy]-2-propanol, in the form of a racemate, an optical antipode or a pharmaceutically acceptable non-toxic acid addition salt thereof.

4. 1-[4-[1,6-dihydro-1-methyl-6-oxo-2-pyridinyloxy]-phenoxy]-3-[2-(3-carbamoyl-4-hydroxy-phenoxy)-ethylamino]-2-propanol, in the form of a racemate, an optical antipode or a pharmaceutically acceptable non-toxic acid addition salt thereof.

5. 1-[2-(3-carbamoyl-4-hydroxy-phenoxy)-ethylamino]-3-[4-(1-methyl-3-methylsulphonyl-1H-1,2,4-triazol-5-yl)-phenoxy]-2-propanol, in the form of a racemate, an optical antipode or a pharmaceutically acceptable non-toxic acid addition salt thereof.

6. 1-[2-(3-carbamoyl-4-hydroxy-phenoxy)-ethylamino]-3-[4-(1-methyl-3-methylthio-1H-1,2,4-triazol-5-yl)-phenoxy]-2-propanol in the form of a racemate, an optical antipode or a pharmaceutically acceptable non-toxic acid addition salt thereof.

7. A pharmaceutical composition useful as a blocking agent of β-adrenergic receptors in the treatment of angina pectoris, hypertrophic cardiomyopathy and heart rhythm disorders and also as blood-pressure-reducing agent comprising a therapeutically effective amount of a compound of the formula I as defined in claim 1 or a pharmaceutically acceptable non-toxic acid addition salt thereof together with a pharmaceutically acceptable excipient.

8. A pharmaceutical composition having β-receptor stimulating properties useful as a positively inotropically active agent especially as a cardiotonic in the treatment of cardiac muscle insufficiency comprising a therapeutically effective amount of a compound of the formula I as defined in claim 1 or a pharmaceutically acceptable non-toxic acid addition salt thereof together with a pharmaceutically acceptable excipient.

9. A method for the treatment of angina pectoris, hypertrophic cardiomyopathy and heart rhythm disorders and also for blood-pressure reducing in a warm-blooded animal in need of such treatment which comprises the administration thereto of a therapeutically active amount of a compound of the formula I as defined in claim 1 or a pharmaceutically acceptable non-toxic acid addition salt thereof.

10. A method for the treatment of cardiac muscle insufficiency in a warm-blooded animal in need of such treatment which comprises the administration thereto of a therapeutically active amount of a compound of the formula I as defined in claim 1 or a pharmaceutically acceptable non-toxic addition salt thereof.

* * * * *